United States Patent [19]

Cronin et al.

[11] 4,087,552
[45] May 2, 1978

[54] INTERFERON INDUCTION IN ANIMALS BY AMINES

[75] Inventors: Timothy H. Cronin, Niantic; Hermann Faubl, Groton; William W. Hoffman, Mystic; James J. Korst, Old Lyme, all of Conn.

[73] Assignee: Pfizer Inc., New York, N.Y.

[21] Appl. No.: 687,514

[22] Filed: May 18, 1976

Related U.S. Application Data

[60] Division of Ser. No. 541,240, Jan. 15, 1975, abandoned, which is a division of Ser. No. 330,042, Feb. 6, 1973, Pat. No. 3,872,171, which is a continuation-in-part of Ser. No. 146,548, May 24, 1971, abandoned, which is a continuation-in-part of Ser. No. 62,192, Aug. 7, 1970, abandoned.

[51] Int. Cl.² ............... A61K 31/135; A61K 31/205; A61K 31/495
[52] U.S. Cl. .................................. 424/330; 424/316; 424/250
[58] Field of Search ........................... 424/330, 316

Primary Examiner—Jerome D. Goldberg
Attorney, Agent, or Firm—Connolly and Hutz

[57] ABSTRACT

Combating viral infections in vertebrate animals by administering to the animals an amine selected from those having the formulae:

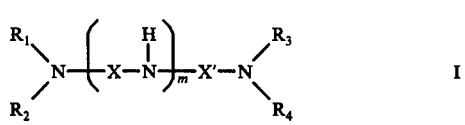

I

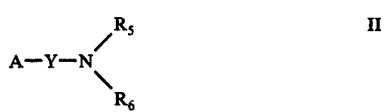

II

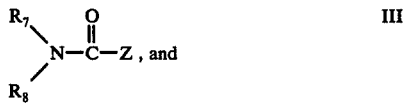

III

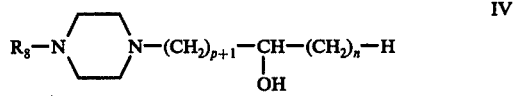

IV and the non-toxic acid addition salts thereof wherein $R_1$ is selected from the group consisting of alkyl of from 1 to 20 carbon atoms, aralkyl, aryloxyalkyl, hydroxyalkyl of from 2 to 8 carbon atoms and

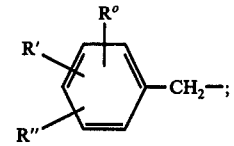

$R_2$ is selected from the group consisting of alkyl of from 12 to 20 carbon atoms, aralkyl and aryloxyalkyl of from 12 to 24 carbon atoms and

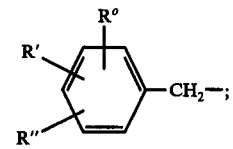

$R^o$ is alkoxy of from 1 to 18 carbon atoms;
each of $R'$ and $R''$ is selected from the group consisting of hydrogen, alkyl, alkoxy of from 1 to 18 carbon atoms; $R'$ and $R''$ when taken together are methylenedioxy;
provided that the total number of carbon atoms in $R^o$, $R'$ and $R''$ is from 5 to 48;
$R_3$ is selected from the group consisting of hydrogen, alkyl of from 1 to 20 carbon atoms, hydroxyalkyl of from 2 to 8 carbon atoms, phenylcarbamoyloxy(lower alkyl), ω-carboxyalkanoyloxy(lower alkyl), allyl, alkanoyl of from 1 to 6 carbon atoms, alkanoyloxy(lower alkyl), carbo(lower alkoxy)lower alkyl, carboxy(lower alkyl), alkoxy(lower alkyl) and gem-di(lower alkoxy)lower alkyl;
$R_4$ is selected from the group consisting of hydrogen, alkyl of from 1 to 8 carbon atoms, hydroxyalkyl of from 2 to 8 carbon atoms, carbo(lower alkoxy)lower alkyl, alkanoyloxy(lower alkyl), carboxy(lower alkyl), alkoxy(lower alkyl), phenyl-carbamoyloxy(lower alkyl), ω-carboxyalkanoyloxy(lower alkyl), allyl, dihydroxyalkyl of from 3 to 8 carbon atoms, and morpholinoethyl; with the proviso that no more than two of the R variables are hydroxyalkyl;
$R_3$ and $R_4$ when taken together with the nitrogen to which they are attached are morpholino;
X is selected from the group consisting of straight chain alkylene of from 2 to 6 carbon atoms and

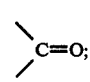

X' is selected from the group consisting of X, phenylenedimethylene and

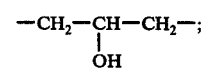

m is 0 or 1, with the provisos that only one of X and X' is

and when X' is phenylenedimethylene, $m$ is 0;

Y is selected from the group consisting of straight chain alkylene of from 2 to 8 carbon atoms and phenylenedimethylene;

A is selected from the group consisting of hydrogen, cyano, hydroxy, alkoxy of from 1 to 20 carbon atoms, alkanoyloxy of from 2 to 20 carbon atoms, phenylcarbamoyloxy, chloro, bromo, ω-carboxyalkanoyloxy(lower alkyl), alkanoyloxy of from 1 to 6 carbon atoms, carbo(lower alkoxy) and alkanoylthio of from 2 to 20 carbon atoms and alkylthio of from 1 to 20 carbon atoms;

$R_5$ is selected from the group consisting of hydrogen, alkyl of from 1 to 20 carbon atoms, hydroxyalkyl of from 2 to 8 carbon atoms, (lower alkoxy)lower alkyl and

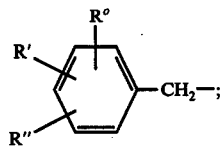

$R_6$ is selected from the group consisting of hydrogen, alkyl of from 12 to 20 carbon atoms, hydroxyalkyl of from 2 to 8 carbon atoms, (lower alkoxy)lower alkyl and

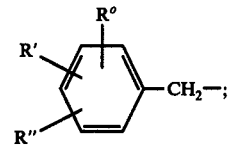

$R_7$ is selected from the group consisting of alkyl of from 12 to 20 carbon atoms and

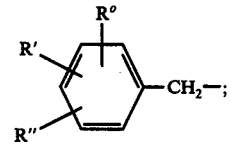

$R_8$ is selected from the group consisting of alkyl of from 1 to 20 carbon atoms and

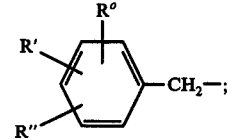

each of $p$ and $n$ is 0 or an integer from 1 to 6, with the proviso that the sum of $p$ and $n$ is no greater than 6; and Z is selected from the group consisting of ω-carboxy(lower alkyl), morpholino, piperidino, piperazino, N-(ω-hydroxy lower alkyl)piperazino and N-(lower alkyl)piperazino.

4 Claims, No Drawings

INTERFERON INDUCTION IN ANIMALS BY AMINES

This application is a division of application Ser. No. 541,240 filed Jan. 15, 1975, now abandoned, which is a division of application Ser. No. 330,042 filed Feb. 6, 1973 now U.S. Pat. No. 3,872,171, which is a continuation in part of application Ser. No. 146,548 filed May 24, 1971 now abandoned, which is a continuation in part of application Ser. No. 62,192 filed Aug. 7, 1970 now abandoned.

BACKGROUND OF THE INVENTION

This invention relates to a novel method for combating viral infections in vertebrate animals which comprises administering to the animals a monoamine, a diamine or a triamine. More particularly, it relates to combating viral infections in vertebrate animals by parenteral, intranasal or topical administration of a substituted aliphatic primary amine, a substituted alkanediamine, a substituted nitrogen-containing heterocyclic compound or a triamine compound.

The cells of vertebrates produce, in response to virus infection, a substance which enables cells to resist the multiplication of a variety of viruses. The viral-resisting or viral-interfering substances are referred to as "interferons." They are a heterogeneous group of antiviral proteins which vary quite widely in their molecular weights. Although such proteins may differ in their physico-chemical properties, they all exhibit the same biological properties; namely, they inhibit a wide range of unrelated viruses, have no toxic or other deleterious effects on cells, and are species-specific (Lockart, *Frontiers of Biology*, Vol. 2, "Interferons," edited by Fintner, W. B. Saunder Company, Philadelphia, 1966, pp. 19–20).

This discovery, by Isaacs and Lindenmann, in 1957 (Proc. Roy. Soc. B. 147, 258–267) gave rise to great optimism that an economic preparation of exogeneous interferon might be developed for routine clinical use against viral infections. However, despite great expenditures of effort and money, no safe, effective, economical source has yet been developed. An alternate approach to producing interferon has, therefore, been pursued. This approach comprises administering to the animal to be protected, or treated, a non-viral substance which stimulates —or induces— production of interferon in the cells. The interferon produced in this fashion is referred to as "endogeneous" interferon.

The discovery of antiviral compounds is far more complicated and difficult than is the discovery of antibacterial and antifungal agents. This is due, in part, to the close structural similarity of viruses and the structures of certain essential cellular components such as ribonucleic and deoxyribonucleic acids, and to the difficulty of establishing suitable tests for evaluating antiviral agents. However, despite these difficulties, numerous non-viral substances have been found capable of stimulating or inducing interferon formation in animals. Included among such substances are bacteria, parasites, bacterial endotoxins, pyran copolymers, helenine, phytohemagglutinin, polyacrylic compounds, nucleic aids and polynucleotides. Use of these inducers is, however, objected to for one or more reasons, e.g., toxicity, antigenicity, infectiousness, and their routine clinical use appears remote (Zhdanov et al., Internat'l. Virol. I, 1st Int. Congr. Virol. Helsinki 1968, S. Karger, New York, pp. 100–1, 1969).

More recently 2,7-bis[2-(diethylamino)ethoxy]fluorene-9-one dihydrochloride, a purely synthetic material of relatively low molecular weight, has been reported to be an oral inducer of interferon in mice (Abstracts Federation Proceedings, Vol. 29, No. 2, page 635, 1970; Abstracts 2189 and 2190).

A variety of "antiviral agents" are described in the literature. These have been summarized by Osdene in "Topics in Medicinal Chemistry," edited by Rabinowitz and Myerson, Interscience Publishers, New York, 1968, pages 141-171. For the purpose of his review, Osdene has made use of Herrmann's definition of "antiviral agent" (Hermann et al., Proc. Soc. Exptl. Biol. Med. 103, 625, 1960); namely, an agent "which can produce either a protective or therapeutic effect to the clear detectable advantage of the virus infected host, or any material that can significantly enhance antibody formation, improve antibody activity, improve non-specific resistance, speed convalescence or depress symptoms." This definition is of such breadth as to cover both prophylactic and therapeutic agents. It includes substances such as interferon, and a host of synthetic materials, such as 1-adamantanamine, pyrimidines, biguanides, guanidine, pteridines to mention a few. It is noted that such synthetic materials are antiviral agents. They are not interferon inducers but operate by a totally different mechanism. Interferon inducers may, of course, be referred to as antiviral agents. The converse, however, is not true.

Virus infections which attack animals, including man, are normally contagious afflictions which may spread so rapidly that they can reach explosive epidemic proportions in relatively short periods of time. In the past, many of these epidemics have resulted in large numbers of deaths and have been responsible for huge economic losses. Obviously a method of reducing the incidence of these viral infections, such as the method of this invention, would be welcome as an addition to the armamentarium of medical technology.

SUMMARY OF THE INVENTION

It has now been found that certain monoamines and diamines, including heterocyclic amines having one or two nitrogen atoms in the ring, and triamines are capable of combating viral infections in vertebrate animals when administered by the parenteral, intranasal and topical routes. The compounds of this invention, many of which are novel, have the formulae

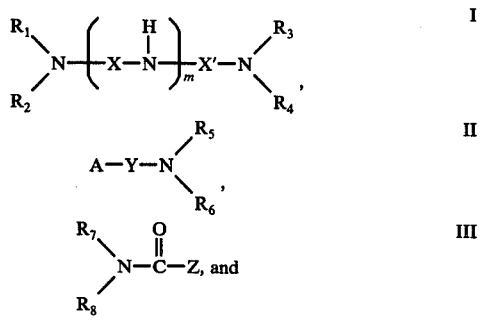

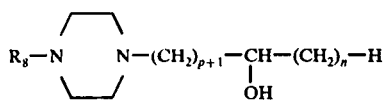 IV and the non-toxic acid addition salts thereof wherein $R_1$ is selected from the group consisting of alkyl of from 1 to 20 carbon atoms, aralkyl, aryloxyalkyl, hydroxyalkyl of from 2 to 8 carbon atoms and

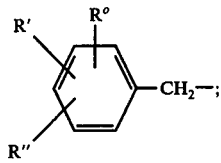

$R_2$ is selected from the group consisting of alkyl of from 12 to 20 carbon atoms, aralkyl and aryloxyalkyl of from 12 to 24 carbon atoms and

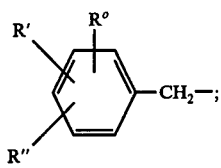

$R^o$ is alkoxy of from 1 to 18 carbon atoms;
each of R' and R" is selected from the group consisting of hydrogen, alkyl and alkoxy of from 1 to 18 carbon atoms; R' and R" when taken together are methylenedioxy;
provided that the total number of carbon atoms in $R^o$, R' and R" is from 5 to 48;
$R_3$ is selected from the group consisting of hydrogen, alkyl of from 1 to 20 carbon atoms, hydroxyalkyl of from 2 to 8 carbon atoms, phenylcarbamoyloxy(lower alkyl), ω-carboxyalkanoyloxy(lower alkyl), allyl, alkanoyl of from 1 to 6 carbon atoms, alkoxy(lower alkyl), gem-di(lower alkoxy)lower alkyl, alkanoyloxy(lower alkyl), carbo(lower alkoxy)lower alkyl, and carboxy(lower alkyl);
$R_4$ is selected from the group consisting of hydrogen, alkyl of from 1 to 8 carbon atoms, hydroxyalkyl of from 2 to 8 carbon atoms, carbo(lower alkoxy)lower alkyl, alkanoyloxy(lower alkyl), carboxy(lower alkyl), alkoxy(lower alkyl), phenyl-carbamoyloxy(lower alkyl), ω-caboxyalkanoyloxy(lower alkyl), allyl, dihydroxyalkyl of from 3 to 8 carbon atoms and morpholinoethyl; with the proviso that no more than two of the R variables are hydroxyalkyl;
$R_3$ and $R_4$ when taken together with the nitrogen to which they are attached are morpholino;
X is selected from the group consisting of straight chain alkylene of from 2 to 6 carbon atoms and

X' is selected from the group consisting of X, phenylene-dimethylene, and

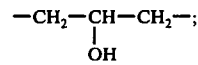

m is 0 or 1, with the provisos that only one of X and X' is

and when X' is phenylenedimethylene, m is 0;
Y is selected from the group consisting of straight chain alkylene of from 2 to 8 carbon atoms and phenylenedimethylene;
A is selected from the group consisting of hydrogen, cyano, hydroxy, alkoxy of from 1 to 20 carbon atoms, alkanoyloxy of from 2 to 20 carbon atoms, phenylcarbamoyloxy, chloro, bromo, ω-carboxyalkanoyloxy(lower alkyl), alkanoyloxy of from 1 to 6 carbon atoms, carbo(lower alkoxy) and alkanoylthio of from 2 to 20 carbon atoms and alkylthio of from 1 to 20 carbon atoms;
$R_5$ is selected from the group consisting of hydrogen, alkyl of from 1 to 20 carbon atoms, hydroxyalkyl of from 2 to 8 carbon atoms, (lower alkoxy)lower alkyl and

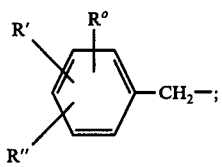

$R_6$ is selected from the group consisting of hydrogen, alkyl of from 12 to 20 carbon atoms, hydroxyalkyl of from 2 to 8 carbon atoms, (lower alkoxy)lower alkyl and

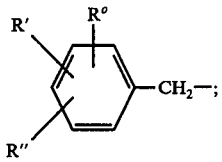

$R_7$ is selected from the group consisting of alkyl of from 12 to 20 carbon atoms and

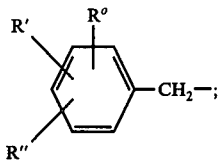

$R_8$ is selected from the group consisting of alkyl of from 1 to 20 carbon atoms and

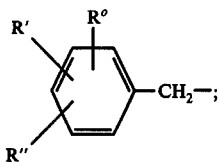

each of p and n is 0 or an integer from 1 to 6, with the proviso that the sum of p and n is no greater than 6; and Z is selected from the group consisting of ω-carboxy(lower alkyl), morpholino, piperidino, piperazino, N-(ω-hydroxy lower alkyl)piperazino and N-(lower alkyl)piperazino.

Of the lower alkoxy, lower alkyl and carbo(lower alkoxy) groups, those having up to four carbon atoms in the alkoxy and alkyl groups are preferred since the starting materials are readily available. The term "phenylenedimethylene" includes, of course, the three isomeric, that is, the o-, the m- and the p- phenylenedimethylene groups.

By "non-toxic" acid addition salts is meant those salts which are non-toxic at the dosages administered. The non-toxic acid addition salts of the above-mentioned bases which may be employed are the water-soluble and water-insoluble salts such as the hydrochloride, hydrobromide, phosphate, nitrate, sulfate, acetate, hexafluorophosphate, citrate, gluconate, benzoate, propionate, butyrate, sulfosalicylate, maleate, laurate, maleate, fumarate, succinate, oxalate, tartrate, amsonate (4,4'-diaminostilbene-2,2'-disulfonate), pamoate (1,1'-methylene-bis-2-hydroxy-3-naphthoate), stearate, 3-hydroxy-2-naphthoate, p-toluenesulfonate, picrate, lactate and suramin salt.

In addition to the above compounds, compounds of formulae I and II wherein (a) the X, X' and Y variables represent straight chain alkylene radicals of up to 13 carbon atoms, or branched-chain alkylene groups of 3 to 13 carbon atoms; (b) X, X' and Y are arylene, e.g., phenylene, naphthylene, anthrylene, biphenylene or —(CH$_2$)$_x$-arylene-(CH$_2$)$_y$—wherein x and y are integers from 1 to 4; (c) those wherein one or more of the R variables represent unsaturated alkyl radicals having from 2 to 20 carbon atoms and from 1 to 3 double bonds; polyhydroxyalkyl; aryl (phenyl, naphthyl); aralkyl (benzyl, phenethyl, phenylpropyl); phenoxyalkyl and substituted derivatives of the aforementioned aryl, aralkyl and phenoxyalkyl wherein the substituent is in the aryl moiety and is alkyl, chloro, bromo, alkoxy or carbo (lower alkoxy); (d) compounds of formulae I and II wherein the R groups together with the nitrogen atoms to which they are attached form a heterocyclic structure wherein the heterocyclic moiety contains from 3 to 7 carbon atoms and wherein the hetero atom is at least one of N, O, or S, such as morpholino, thiomorpholino, piperidino, piperazino, N-lower alkyl piperazino, N-(hydroxy lower alkyl)-piperazino, pyrrolo, pyrolidino, 2-(lower carbalkoxy)pyrrolidino, indolo, benzimidazolo, 1 -benzotriazolo, 2,1,3-benzothiazole, pyrazolo, phenoxazino, azetidine; azepino; tetrazolo; an azacycloalkane such as azacyclooctadecane; 10,11-dihydro-5H-dibenz[b,f]azepino; a triazepino, e.g., 1,3,5-triazepino, and 11-dibenzo[1,2,5]triazepino; (e) and compounds of formula I wherein X or X' represent C=NH or C=S; (f) N-oxides of the compounds of formulae I through IV; (g) and compounds of formula III wherein Z is N-substituted piperazino wherein the substituent is carbalkoxy, acyl or —X'-NR$_3$R$_4$ wherein X', R$_3$ and R$_4$ are as defined above; also combat viral infections when administered to vertebrate animals by the parenteral route.

One preferred group of compounds of Formula I includes those wherein R$_1$ is selected from the group consisting of alkyl of from 1–20 carbon atoms, aralkyl, aryloxyalkyl, and

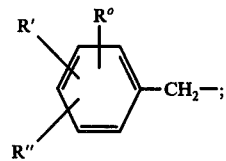

wherein R$^o$ is alkoxy of from 1 to 18 carbon atoms;
each of R' and R" is hydrogen, alkyl or alkoxy of from 1 to carbon atoms; R' and R" when taken together are methylenedioxy;
R$_2$ is selected from the group consisting of alkyl of from 12 to 20 carbon atoms, aralkyl, aryloxyalkyl and

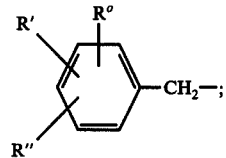

wherein R$^o$ is alkoxy of from 1 to 18 carbon atoms;
each of R' and R" is hydrogen, alkyl or alkoxy of from 1 to 18 carbon atoms; R' and R" when taken together are methylenedioxy;
R$_3$ and R$_4$ are each hydrogen;
m is 0; and
X' is phenylenedimethylene.

The compounds described herein exhibit broad spectrum activity against a variety of viruses in vivo when administered parenterally (subcutaneously, intramuscularly, intraperitoneally), intranasally (e.g. by inhalation or spray) or topically to verebrate animals. This usefulness is primarily one of prophylactic rather than of therapeutic control of virus infections. Although the present invention is not to be construed as limited by such a theory, it is possible that the compounds of this invention function in combating viral infections by virtue of their ability to induce the production of endogenous interferon. They do not produce therferon in tissue culture but only in vivo and can, therefore, be considered as stimulators of host defense mechanisms.

Further, these compounds stimulate the animal body to produce interferon when administered alone and/or in combination with an otherwise inactive, single-stranded ribonucleic acid, such as highly polymerized ribonucleic acid from yeast, yeast nucleic acid (Calbiochem 55712, Calbiochem, Los Angeles, California). Those compounds which induce interferon when administered alone are given at considerably lower doses when given in combination with the single-stranded ribonucleic acid. Particularly useful as inducers of interferon when used alone are compounds of formula I wherein R$_1$ is alkyl of from 1 to 20 carbon atoms; R$_2$ is alkyl of from 12 to 20 carbon atoms; R$_3$ is hydrogen, formyl, alkyl of from 1 to 20 carbon atoms or hydroxyalkyl of from 2 to 4 carbon atoms; $R_4$ is hydrogen or hydroxyalkyl of from 2 to 4 carbon atoms; $X'$ is alkylene of from 3 to 6 carbon atoms or phenylenedimethylene; and m is 0, with the proviso that at least one and not more than two hydroxyalkyl groups are present; compounds of formula I wherein $R_1$, $R_2$, $R_3$ and $R_4$ are as defined immediately above, X is C=O, m is 0 and $X'$ is akylene of from 2 to 6 carbon atoms; compounds of formula II wherein A is hydroxy; Y is straight chain alkylene of 2 to 4 carbon atoms; and $R_5$ and $R_6$ are alkyl of from 12 to 20 carbon atoms; and compounds of formula III wherein Z is N-substituted piperazino and $R_7$ and $R_8$ are each alkyl. An especially preferred group of compounds of formula I includes those in which $R_1$ and $R_2$ are each alkyl of 12 to 20 carbon atoms, $R_3$ and $R_4$ are each hydroxyethyl, $X'$ is straight chain alkylene of from 3 to 5 carbon atoms, and m is 0. Particularly valuable are the following compounds:

N,N-dioctadecyl-N'-formyl-1,3-propanediamine,
N,N-dioctadecyl-N',N'-bis(2-hydroxyethyl)-1,3-propanediamine,
1-dioctadecylaminomethyl-3-aminomethylbenzene,
N,N-dihexadecyl-N',N'-bis(2-hydroxyethyl)-1,4-butanediamine,
N,N-dioctadecyl-N',N'-bis(2-hydroxypropyl)-1,3-propanediamine,
N-(2-hydroxyethyl)dioctadecylamine,
N-(3-hydroxypropyl)dioctadecylamine,
1,1-dioctadecyl-3-(2-[bis(2-hydroxyethyl)amino]ethyl)urea,
1-(N,N-dioctadecylcarbamoyl)-4-methylpiperazine,
1(N,N-dioctadecylcarbamoyl)-4-(2-hydroxyethyl)-piperazine.

The compounds of this invention, many of which are known, are prepared by methods familiar to those skilled in the art.

U.S. Pat. No. 3,235,501, for example, discloses, in theory at least when all combinations and permutations of the several variables are considered, thousands upon thousands of polyoxyalkylated aliphatic amines derived from primary and secondary mono- and diamines. The compounds are produced by alkoxylation (ethoxylation or propoxylation) of primary and secondary mono- and diamines. In such cases, the alkoxylation reaction occurs in a random manner to produce a mixture of alkoxylated compounds in which from 1 to 25 alkylene oxide moieties may be present. Many of the compounds of formula I above fall within the theortcical list of compounds encompassed by this patent. However, despite the extremely broad, indeed infinite, disclosure to polyoxylated aliphatic amines, the patent is completely devoid of reference to specific compounds embraced by formula I above. The innumerable possibilities of the patent disclosure coupled with the ambiguous and vague nature of the method of preparation disclosed, render it unlikely that any specific compound would be suggested to one skilled in the art.

Also disclosed in the literature are compounds of formula III wherein each of $R_7$ and $R_8$ is hydrogen or lower alkyl (Kushner et al., J. Org. Chem. 13, 144–53, 1948; Pressman et al., J. Am. Chem. Soc. 70, 1352–8, 1948). Such compounds do not induce interferon when administered to animals as described herein. Quite unexpectedly, however, it has been found that when at least one of $R_7$ and $R_8$ is alkyl of twelve or more carbon atoms, the compounds do function to combat viral infections.

The basic reaction is the alkylation of an amine, primary or secondary with, for example, an alkyl halide or hydroxyalkyl halide, usually chloride or bromide in an organic solvent in the presence of a base or acid acceptor. Other methods of alkylation can, of course, be employed such as the use of aluminum alkoxides, esters of sulfuric and p-toluenesulfonic acid. Appropriate methods for preparing cc pounds of the above formulae are described by Zook and Wagner, "Synthetic Organic Chemistry," John Wiley & Sons, Inc., New York, 1953, pages 666–670.

Derivatives of 1,3-propanediamine are conveniently made by cyanoethylation of the appropriate primary or secondary amines by conventional methods. The propionitrile compound ($R_1R_2NCH_2CH_2CN$) thus obtained is then hydrogenated to the corresponding 1,3-propanediamine ($R_1R_2NCH_2CH_2CH_2NH_2$) by well-known methods, e.g., hydrogenation over Raney nickel.

Acylated amines are readily prepared by treating the appropriate amine with an acyl halide or anhydride in the presence of a base according to procedures well known to those skilled in the art.

An alternative method for preparing compounds of formulae I and II having N-hydroxyalkyl groups comprises treating a hydroxyalkyl reactant, e.g., an N,N-dialkylamino alkanol, with methane sulfonyl chloride and then reacting the reaction mixture with the appropriate hydroxyalkylamine or di(hydroxyalkyl)amine.

Urea derivatives of formulae I and III are also prepared by conventional methods as by reaction of a carbamyl chloride ($R_1R_2NCOCl$) with an amino reactant $H_2N-X'-NR_3R_4$ or N-substituted piperazine in an organic solvent in the presence of an acid acceptor which can, of course, be an excess of the amine reactant.

Compounds of formula I wherein the $X'$ variable is phenylenedimethylene are prepared by standard procedures from cyanobenzylbromides or chlorides. The appropriate amine, e.g. $R_1R_2NH$, is benzylated with a cyanobenzylbromide or chloride and the cyanobenzylamine compound produced reduced to the corresponding aminomethylbenzylamine derivative. The aminomethyl group ($-CH_2NH_2$) is then treated, e.g., alkylated, with appropriate reactants to convert it to $-CH_2NR_3R_4$. Compounds of formula II wherein Y is phenylenedimethylene are also prepared by benzylation of the appropriate amine $R_5R_6NH$ with a cyanobenzylbromide (or chloride). The cyanobenzylamine thus produced is converted to an ortho ester which is reduced to an acetal and subsequently hydrolyzed to the aldehyde. Reduction of the aldehyde affords a hydroxymethyl benzylamine. The hydroxymethyl serves as convenient route via known procedures to formula II compounds, and also to formula I compounds, e.g., by halogenation and amination.

The herein-described compounds of formulae I, II and III wherein the $R_1$, $R_2$, $R_5$, $R_6$, $R_7$ or $R_8$ groups are substituted benzyl

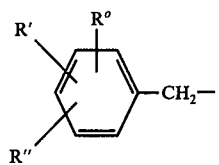

are conveniently produced from appropriate benzaldehydes via reduction to a benzyl alcohol followed by conversion to a benzyl chloride and then amination. Alternatively, the benzaldehyde is reductively aminated to produce, depending upon the conditions, a mono- or dibenzylamine. Utilization of the benzylamine derivatives in conventional reactions as described above affords compounds of formulae I-III.

Acid addition salts of the compounds described herein are prepared by conventional procedures as by mixing the amine compound in a suitable solvent with the required acid and recovering the salt by evaporation or by precipitation by addition of a non-solvent for the salt. Hydrochloride salts are readily prepared by passing dry hydrogen chloride through a solution of the amine compound in an organic solvent such as ether.

The antiviral activity of the above-described materials is determined by the following procedures. In the first procedure, the test compound is administered to mice by the intraperitoneal route eighteen to twenty-four hours prior to challenging the mice with a lethal dose of encephalomyocarditis virus and determining the survival rate ten days after challenge. The procedure in which the drug is given 18 to 24 hours before and at a distinctly different site from virus injection is designed to eliminate local effects between drug and virus and select only compounds which produce a systemic interferon response.

The second general procedure discriminates between compounds which exhibit antiviral activity in the first procedure for their ability to produce an antiviral state in mice as indicated by their ability to stimulate circulating interferon after parenteral administration. In both procedures, the test compounds are administered alone and in combination with from about 2 to about 20 times by weight of an otherwise inactive (non-inducer of interferon and non-antiviral), single-stranded, highly-polymerized ribonucleic acid from yeast, yeast nucleic acid.

DETAILED DESCRIPTION OF THE INVENTION

Parenteral, topical and intranasal administration of the above-described amines to an animal, including man, before exposure of the animal to an infectious virus provide rapid resistance to the virus. The resistance engendered is non-specific and is effective against a great number of viruses. Such administration is effective when given as much as seven days prior to exposure to the virus. Preferably, however, administration should take place from about three days to about one day before exposure to the virus, although this will vary somewhat with the particular animal species and the particular infectious virus.

When administered parenterally the materials of this invention are used at a level of from about 1 mg.kg. of body weight to about 250 mg./kg. of body weight. The favored range is from about 5 mg./kg. to about 100 mg./kg. of body weight, and the preferred range from about 5 mg./kg. to about 50 mg./kg. of body weight. The dosage, of course, is dependent upon the animal being treated and the particular amine compound involved and is to be determined by the individual responsible for its administration. Generally, small doses will be administered initially with gradual increase in dosage until the optimal dosage level is determined for the particular subject under treatment.

Intraperitoneal injections are the preferred method of parenteral injection for several reasons: simplicity, convenience and the compounds appear less toxic. Vehicles suitable for parenteral injection may be either aqueous such as water, isotonic saline, isotonic dextrose, Ringer's solution, or non-aqueous such as fatty oils of vegetable origin (cottonseed, peanut oil, corn, sesame) and other non-aqueous vehicles whicl will not interfere with the efficacy of the preparation and are non-toxic in the volume or proportion used (glycerol, ethanol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol.

When the materials of this invention are administered, they are most easily and economically used in a dispersed form in an acceptable carrier. When it is said that this material is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

In practicing the intranasal route of administration of this invention any practical method can be used to contact the inducer with the respiratory tract of the animal. Effective methods include administration of the inducer by intranasal or nasopharyngeal drops and by inhalation as delivered by a nebulizer or an aerosol. Such methods of administration are of practical importance because they provide an easy, safe and efficient method of practicing this invention. For intranasal administration of the inducer, usually in an acceptable carrier, a concentration of inducer between 1.0 mg./ml. and 100 mg./ml. is satisfactory. Concentrations in the range of about 30 to 50 mg./ml. allow administration of a convenient volume of material.

For topical application the inducers are most conveniently used in an acceptable carrier to permit ease and control of application and better absorption. Here also concentrations in the range of from about 1.0 mg./ml. to about 250 mg./ml. are satisfactory. In general, in the above two methods of administration a dose within the range of about 1.0 mg./kg. to about 250 mg./kg. of body weight and, preferably, from about 5.0 mg./kg. to about 50 mg./kg. of body weight will be administered.

The compounds employed in this invention may be employed alone, i.e., without other medicinals, as mixtures of more than one of the herein-described compounds or in combination with other medicinal agents, such as analgesics, anesthetics, antiseptics, decongestants, antibiotics, vaccines, buffering agents and inorganic salts, to afford desirable pharmacological properties. Further, they may be administered in combination with hyaluronidase to avoid or, at least, to minimize local irritation and to increase the rate of absorption of the compound. Hyaluronidase levels of at least about 150 (U.S.P.) units are effective in this respect although higher or lower levels can, of course, be used.

Those materials of this invention which are water-insoluble, including those which are of low and/or difficult solubility in water, are, for optimum results, administered in formulations, e.g., suspensions, emulsions, which permit formation of particle sizes of less than about 20μ. The particle sizes of the formulations influence their biological activity apparently through better absorption of the active materials. In formulating these materials various surface active agents and protective colloids are used. Suitable surface active agents are the partial esters of common fatty acids, such as lauric, oleic, stearic, with hexitol anhydrides derived from sorbitol, and the polyoxyethylene derivatives of such ester products. Such products are sold under the trademarks "Spans" and "Tweens," respectively, and are available from the Atlas Powder Co., Wilmington, Delaware. Cellulose ethers, especially cellulose methyl ether (Methocel, available from the Dow Chemical Co., Midland, Michigan) are highly efficient as protective colloids for use in emulsions containing the materials of this invention.

The water-soluble materials described herein are administered for optimum results in aqueous solution.

The production of interferon by the administration of compounds described herein is demonstrated by the protection of animals, generally mice as the initial test animal, against viral infections. Encephalomyocarditis virus is a convenient test organism. The challenge virus is prepared by inoculating mice for at least five passages with a neurotropic strain of encephalomyocarditis virus (infected mouse brain). A 10 percent suspension of infected brain tissues is prepared from infected mice and stored at −70° C. until needed (Takano et al., J. Bact. 90, 1542, 1965). It is titrated to a dose which will cause death in five to seven days after challenge to unprotected animals. It is given subcutaneously into the neck scruff. The appropriate dose is contained in 0.1 ml. In general, the dose administered to the animals is from 10 to 25 times the $LD_{50}$(the dose which causes the death of 50 percent of the animals).

For determination of antiviral activity, mice are parenterally (intraperitoneally) injected with the test compound at levels of 5 or 10 mg./kg. and 50 mg./kg. of body weight eighteen to twenty hours prior to virus challenge and the number of survivors determined ten days after challenge. Interferon production is monitored following injection of the test compound according to the procedure described by Wheelock, Proc. Soc. Exptl. Biol. Med. 124, 855–85 (1967).

Once interferon induction by a given compound is observed, the compound is administered to the test animal at various time intervals prior to challenge, e.g., 6, 36, 48 and 72 hours, and by other parenteral routes, e.g., intramuscular and subcutaneous.

The induction of interferon is demonstrated in the following manner. A representative formulation containing N,N-dioctadecyl-N',N'-bis(2-hydroxyethyl)-1,3-propanediamine as the inducer is exemplified.

A mixture of the inducer (100 mg.) and polysorbate 80 (Tween 80; 0.1 ml.) is heated in a boiling water bath. The amine melts and is completely miscible with the polysorbate 80. To this mixture is then added with vigorous vortexing 2.5 ml. of the following composition previously warmed to about 55° C:

| | |
|---|---|
| Methocel-15 (Dow Chemical Co.) | 0.50 g. |
| Tween 80 | >1.00 g. |
| CMC-70* | 10.00 g. |
| Sodium chloride | 9.00 g. |
| Distilled water | 984.00 g. |

*Sodium carboxymethyl cellulose available from Hercules Powder Co., Wilmington, Delaware.

Then 7.28 ml of a 0.14M sodium chloride-0.01M sodium phosphate solution of pH 7.0 warmed at 55° C. is added with continued vigorous vortexing. The formulation thus produced contains 10 mg. of inducer per ml. of suspension.

The hydrochloride salt of N,N-dioctadecyl-N',N'-bis(2-hydroxyethyl)-1,3-propanediamine is readily formulated by vigorous vortexing of the salt in hot 0.14M sodium chloride-0.01M sodium phosphate of pH 7.0.

Interferon induction is determined using female albino Swiss mice (Charles-River) as the test animal. Mice weighing 20 to 25 grams are housed in groups of five and are given food and water ad libitum. The test material is evaluated at 5 mg./kg. and 50 mg/kg. of body weight and given in a single intraperitoneal injection (0.5 ml.) eighteen to twenty hours prior to bleeding. The mice are bled under ether anesthesia from the bracheal artery, the blood collected in heparinized pipettes and tubes, and the pooled plasma from the five mice prepared by centrifugation of the blood for thirty minutes at 2,000 RPM. Dilutions of the plasma are pipetted into plastic tubes containing sheets of L-929 mouse fibroblasts (available from Flow Laboratories, Rockville, Maryland). These latter are twenty-four hour cultures in L-15 media containing 10 percent fetal calf serum and antibiotics (available from Grand Island Biological Company, Grand Island, New York). The cultures are grown from initial plantings of 1 ml. of 100,000 cells/ml. After twenty-four hours of incubation with the plasma, the cultures are washed with media and challenged with 0.2 ml. of a dilution of vesicular stomatitis virus titrated to produce a complete destruction of the cell sheets in 24 to 48 hours. The cultures are in contact with the virus dilution in protein-free media for one hour to allow the virus to adsorb to the cells and then the tubes receive 1 ml. of complete media. After 24 to 48 hours of incubation at 37° C., the tubes are scored for cytopathogenic effect of the virus and compared with standard interferon samples. Interferon units are recorded as the reciprocal of the plasma concentration which affords 50 percent protection to the cell sheets.

The antiviral activity of N,N-dioctadecyl-N',N'-bis(2-hydroxyethyl)-1,3-propanediamine is determined using female albino Swiss mice (Charles-River) as the test animal. Mice weighing 20 to 25 grams are housed in groups of five and are given food and water ad libitum. The test material is evaluated at two dose levels (5 mg./kg. and 50 mg./kg. of body weight) and administered in a single 0.5 ml. intraperitoneal injection eighteen to twenty hours prior to virus challenge. On the following day (eighteen to twenty hours post injection) the mice are challenged subcutaneously with an 0.2 ml. injection of encephalomyocarditis virus at a dilution titrated to give a five- to six-day death endpoint in unprotected animals. Survival data is recorded for the subsequent ten days and the ten-day survival is used as an index of efficacy. Validity of each test is established by the inclusion of unprotected groups and groups receiving pyran co-polymer, 100 mg./kg., for positive control.

The water-soluble compounds of the invention are conveniently administered in phosphate buffered saline. The water-insoluble compounds are administered in formulations of the type described above or in various other formulation as previously noted. Dimethylsulfoxide serves as a suitable vehicle for water-insoluble compounds. A representative formulation for such compounds comprises 25 to 100 mg. of the chosen drug, dimethylsulfoxide (1 ml.), polysorbate 80 (1 ml.) and 8 ml. of a composition comprising

| | |
|---|---|
| Methocel-15 | 0.50 g./l. |
| Polysorbate 80 | 1.00 g./l. |
| CMC-70 | 10.00 g./l. |
| Sodium chloride | 9.00 g./l. |
| Methyl p-hydroxybenzoate | 1.80 g./l. |
| Propyl p-hydroxybenzoate | 0.20 g./l. |
| Distilled water | 984.00 g./l. |

In certain instances, as where clumping of the drug particles occurs, sonication is employed to provide a homogeneous system.

EXAMPLE I

N,N-Dioctadecyl-N',N'-Bis(2-Hydroxyethyl)-1,3-Propanediamine

A mixture of octadecylbromide (666 g., 2.0 moles), N-(3-aminopropyl)-diethanolamine (162 g., 1.0 mole) and potassium carbonate (276 g., 2.0 moles) is stirred vigorously and heated slowly to 120° C. and held at this temperature for one-half hour. The mixture is allowed to cool to 70° C. then 500 ml. of a 1:1 methylene chloride-water mixture added. The mixture is then slowly poured into a stirred mixture of methylene chloride (9.75 liters)-water (9.75 liters). The methylene chloride phase is separated after fifteen minutes and the remaining aqueous phase extracted with methylene chloride (4 liters). The combined methylene chloride extracts are dried over anhydrous magnesium sulfate then stripped to one-half volume under reduced pressure. The concentrate is then stirred with silicic acid (300 g.) for one-half hour, the silicic acid removed and the clear solution slowly poured into acetone (16 liters) containing succinic acid (300 g.). The mixture is cooled slowly to 10° C. and the succinate salt filtered off; 615 g. (68 percent of theory); m.p. 78°-90° C.

It is purified by recrystallization from acetone-methylene chloride (2-1).

The free base is obtained by dissolving the succinate salt (420 g.) in methylene chloride (4 liters) and aqueous sodium hydroxide (2.5 liters of 5 percent solution). The mixture is stirred for fifteen minutes, the methylene chloride phase separated and washed successively with aqueous sodium hydroxide (1 × 18 liters of 5 percent solution), water (3 × 6 liters) and saturated aqueous sodium chloride (1 × 6 liters). It is then dried (MgSO$_4$), filtered and evaporated in vacuo to an oil. The oil is dissolved in acetone (5 liters) at 50° C. and the solution allowed to cool slowly to give a white precipitate (267 g.) m.p. 39°-41° C. Another preparation yielded a somewhat lower melting point of 36-36.8° C.

Additional product (20 g.) is obtained by cooling the filtrate to 0° C. Total yield is 287 g.; 43 percent of theory.

Elemental analysis

| Theory for C$_{43}$H$_{90}$N$_2$O$_2$ | Found: |
|---|---|
| C 77.41 | C 77.42 |
| H 13.60 | H 13.84 |

-continued

| Theory for C$_{43}$H$_{90}$N$_2$O$_2$ | Found: |
|---|---|
| N 4.20 | N 4.16 |

Potentiometric Titration
Solvent: acetic acid
Titrant: 0.5 N perchloric acid in acetic acid
Theory = 333.6 Found = 342.0
Infra-red (1% in KBr)
Major absorption maxima (in microns) at:
3.05, 3.43, 3.52, 6.80, 7.15, 7.25, 7.65, 8.32, 8.39, 8.68, 9.15, 9.24, 9.30, 9.62, 9.70, 11.04, 13.96.

The dilactate salt is prepared by adding two equivalents of lactic acid dissolved in ether to an ether solution of the base, followed by evaporation of the ether; m.p. 50°-52° C. becomes tacky and melts at 60°-62° C.

The diphosphate salt is prepared by adding excess phosphoric acid to a solution of the base in hexane. It is recrystallized from a large volume of methanol; m.p. becomes a gel at 140° C.; brown at 175°-190° C. and melts at 245°-247° C.

The dihydrochloride salt is prepared by bubbling dry hydrogen caloide into an ether solution of the base. The residue obtained by removal of the ether is slurried in acetone, filtered, and recrystallized from ether containing some methanol; m.p. gels at 180°-182° C. and melts completely at 238°-240° C.

EXAMPLE II

N,N-Dioctadecyl-N',N'-Bis(2-Hydroxyethyl)Ethanediamine

A mixture of octadecylbromide (6.66 g., 0.02 mole), N-(2-aminoethyl)-diethanolamine (1.48 g., 0.01 mole) and potassium carbonate (2.76 g., 0.02 mole) is heated at reflux under an atmosphere of nitrogen for two hours. The reaction mixture is then cooled and treated with aqueous sodium hydroxide (50 ml. of 10 percent solution). Ethyl acetate (50 ml.) is added, the mixture thoroughly agitated and the ethylacetate separated, washed with water, and dried over anhydrous magnesium sulfate. Removal of the solvent by evaporation affords the crude product which is recrystallized from ethylacetate or acetone; m.p. 33°-34° C.

The hydrochloride, phosphate, succinate and picrate salts are made by adding the above base to ethylacetate containing stochiometric amounts of the respective acids. The salts are recovered by filtration, washed with cold ethylacetate, and dried.

| Salt | M.P. (° C.) |
|---|---|
| dihydrochloride | 228–30 |
| diphosphate | 102–3 |
| disuccinate | 155–6 |
| dipicrate | 84–6 |

Repetition of the above procedure but using the appropriate (2-hydroxyalkyl)alkanediamine derivative and the appropriate alkyl bromide produces the following compounds:

$$\begin{array}{c} R_1 \\ \diagdown \\ N-(CH_2)_n-N \\ \diagup \\ R_2 \end{array} \begin{array}{c} R_3 \\ \diagup \\ \\ \diagdown \\ R_4 \end{array}$$

| R$_1$ | R$_2$ | R$_3$ | R$_4$ | n | Salt | M.P. (° C.) |
|---|---|---|---|---|---|---|
| C$_{16}$H$_{33}$ | C$_{16}$H$_{33}$ | CH$_2$CH$_2$OH | CH$_2$CH$_2$OH | 2 | 2H$_3$PO$_4$ | 133–5 |

-continued $$\begin{array}{c} R_1 \\ \diagdown \\ N-(CH_2)_n-N \\ \diagup \\ R_2 \end{array} \begin{array}{c} R_3 \\ \diagup \\ \diagdown \\ R_4 \end{array}$$

| $R_1$ | $R_2$ | $R_3$ | $R_4$ | n | Salt | M.P. (° C.) |
|---|---|---|---|---|---|---|
| $CH_2CH_2OH$ | $C_{18}H_{37}$ | $C_{18}H_{37}$ | $CH_2CH_2OH$ | 2 | 2HBr | 236–8 |
| $C_{20}H_{41}$ | $C_{20}H_{41}$ | $CH_2CH_2OH$ | $CH_2CH_2OH$ | 3 | — | 38–45 |
| $C_{20}H_{41}$ | $C_{20}H_{41}$ | $CH_2CH_2OH$ | $CH_2CH_2OH$ | 2 | 2HCl | 188–9 |
| $C_{20}H_{41}$ | $C_{20}H_{41}$ | $CH_2CH_2OH$ | $CH_2CH_2OH$ | 2 | $2H_3PO_4$ | 220–3 |
| $C_{18}H_{37}$ | $C_{18}H_{37}$ | $CH_2CH_2OH$ | $CH_2CH_2OH$ | 4 | — | 51–2 |
| $C_{16}H_{33}$ | $C_{16}H_{33}$ | $CH_2CH_2OH$ | $CH_2CH_2OH$ | 4 | — | 44–5 |
| $C_{14}H_{29}$ | $C_{14}H_{29}$ | $CH_2CH_2OH$ | $CH_2CH_2OH$ | 4 | — | 39 |
| $C_{16}H_{33}$ | $C_{16}H_{33}$ | $-CH_2CH_2-O-CH_2CH_2-$ | | 3 | 2HCl | 167–170 |
| $C_{14}H_{29}$ | $C_{14}H_{29}$ | 3—$CH_2CH_2-O-CH_2CH_2$ | | 3 | 2HCl | 174–7 |
| $C_{18}H_{37}$ | $C_{18}H_{37}$ | $-CH_2CH_2-O-CH_2CH_2-$ | | 3 | 2HCl | 170–1 |
| $C_{18}H_{37}$ | $C_{18}H_{37}$ | $CH_2CH_2OH$ | $CH_2CH_2OH$ | 5 | — | 32–3 |
| $C_{18}H_{37}$ | $C_{18}H_{37}$ | $CH_2CH_2OH$ | $CH_2CH_2OH$ | 6 | — | 49–50 |

EXAMPLE III

N,N-Dioctadecyl-1,3-Propanediamine

A. A two-gallon autoclave is charged with 3-(dioctadecylamino)propionitrile (100 g.), ethanol (3750 ml.) containing anhydrous ammonia (100 g.) and Raney nickel (20 g. dry basis) and purged with nitrogen, then with hydrogen. It is then sealed and the hydrogen pressure raised to 250 psi. The autoclave is agitated, the temperature raised to 70° C. and the mixture held at this temperature for 1.5 hours at which time hydrogen absorption has ceased. The autoclave is cooled to 20° C., vented, and the contents removed. The catalyst is filtered off, washed with ethanol, and the combined washings and reaction mixture concentrated in vacuo to a viscous green-yellow oil (82 g.) which solidified upon standing; m.p. 39°–41° C.

Analysis: Calc'd. for $C_{39}H_{82}N_2$: C, 80.97; H, 14.17; N, 4.44 percent.

Found: C, 80.60; H, 14.17; N, 4.79 percent.

3-(Dioctadecylamino)propionitrile is prepared by refluxing a mixture of dioctadecylamine (200 g.) and acrylonitrile (1903.8 ml.) for eighteen hours. The mixture is then concentrated to a waxy semi-solid which is slurried in acetone, filtered, and air dried overnight.

B. The monoacyl derivatives of N,N-dioctadecyl-1,3-propanediamine are prepared as follows:

To a solution of methylene chloride (500 ml. per 0.1 mole of reactants) containing equimolar amounts of N,N-dioctadecyl-1,3-propanediame and triethylamine and cooled in an ice-bath is added an equimolar amount of the appropriate acyl chloride in methylene chloride (25 ml. per 0.1 mole of acyl chloride) over a period of fifteen minutes. The mixture is stirred for ten minutes then brought to room temperature and stirred for one hour. The methylene chloride phase is separated and extracted with water (3 × 25 ml.). The water extract is in turn extracted with methylene chloride (2 × 25 ml.) and the combined methylene chloride phases dried ($Na_2SO_4$) then evaporated under reduced pressure. The residue is taken up in benzene and the solution passed through a silica gel column. The column is eluted with benzene, then with benzene containing increasing amounts of ethyl acetate; e.g., 5, 10, 25, and 50 percent. The eluate is subjected to thin layer chromatography (ethyl acetate) and those fractions which slow only one spot, combined and evaporated.

The following are thus prepared:
N-acetyl derivative M.P. 50°–52° C.
N-propionyl derivative M.P. 48.5°–49° C.

In like manner, the following compounds are prepared from appropriate reactants:

$$\begin{array}{c} R_1 \\ \diagdown \\ N-(CH_2)_3-N \\ \diagup \\ R_2 \end{array} \begin{array}{c} O \\ \| \\ C-R_{3'} \\ \diagdown \\ H \end{array}$$

| $R_1$ | $R_2$ | $R_{3'}$ |
|---|---|---|
| $C_{18}H_{37}$ | $C_{18}H_{37}$ | $C_3H_7$ |
| $C_{18}H_{37}$ | $C_{18}H_{37}$ | $C_5H_{11}$ |
| $C_{16}H_{33}$ | $C_{16}H_{33}$ | H |
| $C_{16}H_{33}$ | $C_{16}H_{33}$ | $CH_3$ |
| $CH_3$ | $C_{12}H_{25}$ | $C_2H_5$ |
| $CH_3$ | $C_{12}H_{25}$ | H |

C. Formyl derivatives are prepared as follows:
N,N-dioctadecyl-N'-formyl-1,3-propanediamine A mixture of N,N-dioctadecyl-1,3-propanediamine (4.88 g.), ethanol (15 ml.) and methyl formate (35 ml.) is heated at reflux for one-half four. By-product methanol is distilled off and additional methyl formate (20 ml.) added. The mixture is refluxed for a half hour and allowed to stand overnight. It is taken to dryness under reduced pressure and the white solid residue recrystallized from ethyl acetate. Yield = quantitative: m.p. 42°–46° C.

EXAMPLE IV

N-(2-Hydroxyethyl)-N',N'-Dioctadecyl-1,3-Propanediamine

To a stirred solution of N,N-dioctadecyl-3-aminopropanol (1.16 g., 2 mM.) in chloroform (30 ml.) is added methanesulfonyl chloride (0.285 g., 2.5 mM.) and the mixture stirred for seventy-five minutes. Ethanolamine (1.22 g., 20 mM.) is added and the mixture refluxed for forty-five minutes, then cooled and diluted with chloroform (200 ml.). The chloroform solution is washed successively with aqueous sodium hydroxide (5 percent), water and saturated aqueous sodium chloride. It is then dried ($Na_2SO_4$) and concentrated to a waxy solid.

Picrate Salt: The free base is dissolved in ethanol (100 ml.) and a solution of picric acid (2 g.) in ethanol (20 ml.) added. The salt precipitates upon chilling the solution. It is filtered off, washed with cold ethanol and dried, 1.2 g., m.p. 149°–151° C. Recrystallization from hot ethanol raises the melting point to 150°–152° C.

In like manner, the following compounds are prepared using appropriate reactants ($HNR_3R_4$) in place of ethanolamine. The hydrochloride salts are prepared by bubbling excess dry hydrogen chloride gas into a chloroform solution of the free base and the salt recovered by evaporation of the solvent.

EXAMPLE VI

N,N-Bis(2-Hydroxyethyl)-N'-Octadecyl-1,3-Propanediamine $$\begin{array}{c} C_{18}H_{37} \\ \phantom{C_{18}H_{37}}\diagdown \\ \phantom{XXX} N-CH_2-CH_2-CH_2-N \\ \phantom{C_{18}H_{37}}\diagup \\ C_{18}H_{37} \end{array} \begin{array}{c} R_3 \\ \diagdown \\ \\ \diagup \\ R_4 \end{array}$$

| $R_3$ | $R_4$ | Salt | M.P. (° C.) |
|---|---|---|---|
| H | $CH_2CH_2CH_2OH$ | picrate | 121–2 |
| H | $CH_2CH(OH)CH_2OH$ | picrate | 39–41 |
| H | $n\text{-}C_3H_7$ | picrate | 64–6 |
| H | $n\text{-}n\text{-}C_6H_{13}$ | HCl | 119–22 |
| H | $n\text{-}C_7H_{15}$ | HCl | 53–7 |
| H | $CH_2CH_2OCH_3$ | HCl | 96–9 |
| H | $CH_2CH_2OC_2H_5$ | HCl | 90–4 |
| H | $CH_2CH(OCH_3)_2$ | HCl | 83–8 |
| H | $(CH_2)_3N(CH_2CH_2OH)_2$ | picrate | 116–8 |
| H | $(CH_2)_3NH(CH_2CHOHCH_3)$ | picrate | 105–10 |
| H | $CH_2CHOHCH_2N(C_2H_5)_2$ | HCl | 115–7 |
| $C_2H_5$ | $C_2H_5$ | picrate | 108–10 |
| $n\text{-}C_4H_9$ | $n\text{-}C_4H_9$ | picrate | 66–7 |
| $CH_3$ | $CH_2CH_2OH$ | picrate | 80–2 |
| $n\text{-}C_4H_9$ | $CH_2CH_2OH$ | picrate | 48–52 |
| $CH_2CHOHCH_3$ | $CH_2CHOHCH_3$ | — | (an oil) |
| $CH_2CHOHCH_3$ | $CH_2CHOHCH_3$ | HCl | 52–4; 98–101 |
| H | $CH_2CH_2\text{-morpholino}$ | — | 55–67; 90 |
| H | $CH_2CH_2\text{-morpholino}$ | HCl | 137 |
| H | $CH(CH_3)CH_2COOC_2H_5$ | HCl | 56–79 |
| H | $(CH_2)_4\text{—}OH$ | — | 34–34.5 |
| H | $(CH_2)_4\text{—}OH$ | picrate | 84–6; 94 |
| H | $(CH_2)_5\text{—}OH$ | — | 35–6 |
| H | $(CH_2)_5\text{—}OH$ | picrate | 65–70; 85–90 |
| $C_2H_5$ | $CH_2CH_2OH$ | picrate | 80–6 |
| $CH_3$ | $(CH_2)_4\text{—}OH$ | — | 91–4 |
| $CH_2COOH$ | $CH_2COOH$ | — | 75–90 |
| $CH_2COOCH_3$ | $CH_2COOCH_3$ | — | 75–7 |
| $(CH_2)_3OH$ | $(CH_2)_3OH$ | — | 41–3 |
| $(CH_2)_3OH$ | $(CH_2)_3OH$ | picrate | 91–5; 100–5 |

EXAMPLE V

N,N-Dioctadecyl-N',N'-Diallyl-1,3-Propanediamine

A slurry of N,N-dioctadecyl-1,3-propanediamine (2.895 g., 5 mM.), allyl bromide (4.3 ml., 50 mM.), potassium carbonate (2.0 g.) and methylene chloride (10 ml.) is stirred at room temperature for three hours. The mixture is then cooled in an ice-bath, filtered, and the filtrate chromatographed on acid-washed silica gel. The product is eluted with 5 percent methanol-95 percent ethylacetate and the free base recovered by evaporation of Example IV, melts at 86°–88° C.

Repetition of this procedure but substituting methyl bromoacetate for allyl bromide produces N,N-dioctadecyl-N',N'-bis(carbomethoxymethyl)-1,3-propanediamine. Its hydrochloride, prepared by the procedure of Example IV, melts at 75°–77° C.

The following compounds are similarly prepared from appropriate reactants:

$$\begin{array}{c} R_1 \\ \diagdown \\ \phantom{X} N-(CH_2)_n-N \\ \diagup \\ R_2 \end{array} \begin{array}{c} R_3 \\ \diagdown \\ \\ \diagup \\ CH_2-CH=CH_2 \end{array}$$

| $R_1$ | $R_2$ | $R_3$ | $n$ |
|---|---|---|---|
| $C_{16}H_{33}$ | $C_{16}H_{33}$ | $-CH_2-CH=CH_2$ | 2 |
| $C_{20}H_{41}$ | $C_{20}H_{41}$ | $-CH_2-CH=CH_2$ | 3 |
| $CH_3$ | $C_{16}H_{33}$ | $-CH_2-CH=CH_2$ | 2 |
| $C_{18}H_{37}$ | $C_{18}H_{37}$ | $-CH_2-CH=CH_2$ | 6 |
| $C_{18}H_{37}$ | $C_{18}H_{37}$ | $n\text{-}C_3H_7$ | 3 |
| $C_{18}H_{37}$ | $C_{18}H_{37}$ | $-CH_2CH_2OCH_3$ | 3 |
| $C_{18}H_{37}$ | $C_{18}H_{37}$ | $-CH_2CH_2\text{—morpholino}$ | 3 |
| $C_{18}H_{37}$ | $C_{18}H_{37}$ | $-CH_2CH(OCH_3)_2$ | 3 |
| $C_{18}H_{37}$ | $C_{18}H_{37}$ | $-CH_2CH_2OCOCH_3$ | 3 |
| $C_{18}H_{37}$ | $C_{18}H_{37}$ | $-CH_2CH_2OCONHC_6H_5$ | 3 |

A solution of octadecyl bromide (26.65 g., 80 mM.), N-(3-aminopropyl)diethanolamine (105 g., 640 mM.) and benzyl alcohol (120 ml.) is heated at 130° C. for twenty-three hours. The benzyl alcohol is removed in vacuo (0.1 m. Hg, and 75° C.) and the residue taken up in methylene chloride (250 ml.). The methylene chloride solution is washed with aqueous sodium hydroxide (1N) then with brine. It is dried (Na₂SO₄), concentrated, and distilled; b.p. 242°–246° C. at 0.1 mm Hg. The product is a waxy solid.

EXAMPLE VII

N,N-Bis(2-Hydroxyethyl)-N'-(n-Butyl)-N'-Octadecyl-1,3-Propanediamine

A mixture of N,N-bis(2-hydroxyethyl)-N'-octadecyl-1,3-propanediamine (500 mg., 1.2 mM.), n-butyl bromide (164 mg., 1.2 mM.) and potassium carbonate (160 mg., 1.2 mM.) is heated at 100° C. for 2 hours then at 130° C. for two more hours. The mixture is cooled, taken up in chloroform (100 ml.) and the chloroform solution washed successively with 5 percent aqueous sodium hydroxide (100 ml.), water and brine, then dried (Na₂SO₄). Removal of the chloroform provides the free base (540 mg.).

The picrate salt, prepared by the procedure of Example IV, melts at 85°–87° C.

In like manner, N,N-bis(2-hydroxyethyl)-N'-(n-propyl)-N'-octadecyl-1,3)propanediamine is prepared from n-propylbromide. Its picrate salt melts at 105°–106° C.

The following compounds and their picrate salts are prepared in like manner by alkylation of the products of Examples IV and VI with the appropriate reactant:

$$\begin{array}{c} R_1 \diagdown \quad \diagup R_3 \\ N-(CH_2)_n-N \\ R_2 \diagup \quad \diagdown R_4 \end{array}$$

| R$_3$ | R$_4$ | R$_2$ | R$_1$ | n |
|---|---|---|---|---|
| CH$_2$CH$_2$OH | CH$_2$CH$_2$OH | C$_{18}$H$_{37}$ | C$_{12}$H$_{25}$ | 6 |
| (CH$_2$)$_4$OH | (CH$_2$)$_4$OH | C$_{18}$H$_{37}$ | CH$_3$ | 3 |
| (CH$_2$)$_4$OH | (CH$_2$)$_4$OH | C$_{18}$H$_{37}$ | CH$_6$H$_{13}$ | 3 |
| (CH$_2$)$_4$OH | (CH$_2$)$_4$OH | C$_{18}$H$_{37}$ | CH$_3$ | 6 |
| (CH$_2$)$_4$OH | (CH$_2$1 )$_4$OH | C$_{18}$H$_{37}$ | C$_8$H$_{17}$ | 6 |
| (CH$_2$)$_8$OH | (CH$_2$)$_8$OH | C$_{18}$H$_{37}$ | C$_{18}$H$_{37}$ | 3 |
| (CH$_2$)$_8$OH | (CH$_2$)$_8$OH | C$_{18}$H$_{37}$ | n-C$_4$H$_9$ | 3 |
| (CH$_2$)$_8$OH | (CH$_2$)$_8$OH | C$_{18}$H$_{37}$ | C$_{16}$H$_{33}$ | 5 |
| CH$_2$Ch$_2$CH$_2$OH | CH$_2$CH$_2$CH$_2$OH | C$_{16}$H$_{33}$ | CH$_3$ | 2 |
| CH$_2$CH$_2$CH$_2$OH | CH$_2$CH$_2$CH$_2$OH | C$_{18}$H$_{37}$ | CH$_3$ | 5 |
| (CH$_2$)$_6$OH | (CH$_2$)$_6$OH | C$_{18}$H$_{37}$ | CH$_2$—CH=CH$_2$ | 2 |
| (CH$_2$)$_6$OH | (CH$_2$)$_6$OH | C$_{18}$H$_{37}$ | CH$_2$—C≡CH$_2$ | 5 |
| CH$_2$CH$_2$OH | CH$_2$CH$_2$OH | C$_{20}$H$_{41}$ | C$_6$H$_5$CH$_2$ | 3 |
| CH$_2$CH$_2$OH | CH$_2$CH$_2$OH | C$_{12}$H$_{25}$ | C$_6$H$_5$OCH$_2$ | 3 |
| CH$_2$CH$_2$OH | CH$_2$CH$_2$OH | C$_{16}$H$_{33}$ | C$_6$H$_5$OCH$_2$ | 6 |
| CH$_2$CH(OH)CH$_3$ | CH$_2$CH(OH)CH$_3$ | C$_{14}$H$_{29}$ | C$_6$H$_5$OCH$_2$ | 5 |
| CH$_2$CH$_2$OH | CH$_2$CH$_2$OH | C$_{18}$H$_{37}$ | CH$_2$CH$_2$OCH$_3$ | 3 |
| CH$_3$ | (CH$_2$)$_4$OH | C$_{18}$H$_{37}$ | C$_{18}$H$_{37}$ | 3 |
| i-C$_3$H$_7$ | (CH$_2$)$_5$OH | C$_{18}$H$_{37}$ | C$_{18}$H$_{37}$ | 3 |
| C$_2$H$_5$ | CH$_2$CH(OCH$_3$)$_2$ | C$_{18}$H$_{37}$ | C$_{18}$H$_{37}$ | 3 |
| CH$_2$—CH=CH$_2$ | CH(CH$_3$)CH$_2$<br>\|<br>C$_2$H$_5$O—C=O | C$_{18}$H$_{37}$ | C$_{18}$H$_{37}$ | |
| C$_6$H$_{13}$ | CH(CH$_3$)CH$_2$<br>\|<br>C$_2$H$_5$O—C=O | C$_{18}$H$_{37}$ | C$_{18}$H$_{37}$ | 3 |
| C$_6$H$_5$O(CH$_2$)$_2$ | CH$_2$CH$_2$OCH$_3$ | C$_{18}$H$_{37}$ | C$_{18}$H$_{37}$ | 3 |

EXAMPLE VIII

N,N-Dioctadecyl-N',N'-Bis[2-(3'-Carboxypropionyloxy)-ethyl]-1,3-Propanediamine

N,N-Dioctadecyl-N',N'-bis(2-hydroxyethyl)-1,3-propanediamine (3.335 g., 5 mM.) is added to a solution of succinic anhydride (9.0 g., 90 mM.) in a mixture of ethylacetate (60 ml.) and acetone (60 ml.) at room temperature. After stirring for three hours, the reaction mixture is cooled in an ice-bath and the precipitate which forms filtered off, washed with cold acetone and dried. Recrystallization from hot acetone-ethylacetate (1:1) gives the ester as a fine white powder (1.783 g.), m.p. 64°-67° C.

The following compounds are prepared from appropriate reactants in like manner.

$$\begin{array}{c} R_1 \diagdown \qquad \diagup (CH_2)_s-O-CO-R \\ N-(CH_2)_n-N \\ R_2 \diagup \qquad \diagdown (CH_2)_s-O-CO-R \end{array}$$

| R$_1$ | R$_2$ | n | s | R |
|---|---|---|---|---|
| C$_{18}$H$_{37}$ | C$_{18}$H$_{37}$ | 3 | 2 | CH$_2$CH$_2$COOH |
| C$_{18}$H$_{37}$ | C$_{18}$H$_{37}$ | 3 | 3 | CH$_2$CH$_2$COOH |
| C$_{18}$H$_{37}$ | C$_{18}$H$_{37}$ | 3 | 2 | (CH$_2$)$_3$COOH |
| C$_{16}$H$_{33}$ | C$_{16}$H$_{33}$ | 3 | 2 | CH$_2$CH$_2$COOH |
| C$_{20}$H$_{41}$ | C$_{20}$H$_{41}$ | 3 | 2 | CH$_2$CH$_2$COOH |
| C$_{14}$H$_{29}$ | C$_{14}$H$_{29}$ | 3 | 2 | CH$_2$CH$_2$COOH |
| C$_{14}$H$_{29}$ | C$_{14}$H$_{29}$ | 3 | 2 | (CH$_2$)$_3$COOH |
| C$_{18}$H$_{37}$ | C$_{18}$H$_{37}$ | 3 | 3 | CH$_2$CH$_2$COOH |
| C$_{18}$H$_{37}$ | C$_{18}$H$_{37}$ | 3 | 8 | CH$_2$CH$_2$COOH |
| C$_{18}$H$_{37}$ | C$_{18}$H$_{37}$ | 3 | 6 | CH$_2$CH$_2$COOH |
| CH$_3$ | C$_{18}$H$_{37}$ | 3 | 3 | CH$_2$CH$_2$COOH |
| CH$_3$ | C$_{18}$H$_{37}$ | 3 | 6 | CH$_2$CH$_2$COOH |
| CH$_3$ | C$_{18}$H$_{37}$ | 3 | 4 | CH$_2$CH$_2$COOH |
| C$_{18}$H$_{37}$ | C$_{18}$H$_{37}$ | 4 | 2 | CH$_2$CH$_2$COOH |
| C$_{20}$H$_{41}$ | C$_{20}$H$_{41}$ | 2 | 2 | CH$_2$CH$_2$COOH |
| C$_{18}$H$_{37}$ | C$_{18}$H$_{37}$ | 6 | 2 | CH$_2$CH$_2$COOH |

EXAMPLE IX

N,N-Dioctadecyl-N',N'-bis(2-Phenylcarbamoyloxyethyl)-1,3-Propanediamine

Phenyl isocyanate (3.85 g.) is added to a warm solution of N,N-dioctadecyl-N',N'-bis(2-hydroxyethyl)-1,3-propanediamine (5.0 g.) in ethylacetate (20 ml.) and the mixture heated to reflux for one hour. The mixture is cooled, then taken to dryness under reduced pressure. The residue is triturated with carbon tetrachloride, filtered, and the filtrate evaporated to dryness. Ethyl acetate (25 ml.) is then added, the mixture cooled, filtered, washed with ethylacetate and dried in vacuo; m.p. 54-6° C.

The following compounds are prepared from appropriate reactants by this procedure:

$$\begin{array}{c} R_1 \diagdown \qquad \diagup (CH_2)_s-O-CO-NH-C_6H_5 \\ N-(CH_2)_n-N \\ R_2 \diagup \qquad \diagdown (CH_2)_s-O-CO-NH-C_6H_5 \end{array}$$

| R$_1$ | R$_2$ | n | s |
|---|---|---|---|
| C$_{18}$H$_{37}$ | C$_{18}$H$_{37}$ | 3 | 3 |
| C$_{16}$H$_{33}$ | C$_{16}$H$_{33}$ | 3 | 2 |
| C$_{20}$H$_{41}$ | C$_{20}$H$_{41}$ | 3 | 2 |
| C$_{14}$H$_{29}$ | C$_{14}$H$_{29}$ | 3 | 2 |
| C$_{18}$H$_{37}$ | C$_{18}$H$_{37}$ | 3 | 3 |
| C$_{18}$H$_{37}$ | C$_{18}$H$_{37}$ | 3 | 8 |
| C$_{18}$H$_{37}$ | C$_{18}$H$_{37}$ | 3 | 6 |
| CH$_3$ | C$_{18}$H$_{37}$ | 3 | 3 |
| CH$_3$ | C$_{18}$H$_{37}$ | 3 | 6 |
| CH$_3$ | C$_{18}$H$_{37}$ | 3 | 4 |
| C$_{18}$H$_{37}$ | C$_{18}$H$_{37}$ | 4 | 2 |
| C$_{18}$H$_{25}$ | C$_{12}$H$_{25}$ | 2 | 2 |
| C$_{18}$H$_{37}$ | C$_{18}$H$_{37}$ | 6 | 2 |

EXAMPLE X

N,N-Dioctadecyl-N',N'-bis(2-Palmitoyloxyethyl)-1,3-Propanediamine

Palmitoyl chloride (2.75 g.) is added all at once to a solution of N,N-dioctadecyl-N',N'-bis(2-hydroxyethyl)-1,3-propanediamine (1.334 g.) in ethylacetate (50 ml.) and chloroform (5 ml.) at room temperature. The mixture is stirred for one hour then dry hydrogen chloride gas bubbled in for two minutes. The temperature rose to 42° C. and the initial precipitate (of the amine salt) which formed dissolved. The mixture is chilled to 5° C. then filtered. The product is washed with ethylacetate and air dried. It is recrystallized from ethylacetate-hexane; m.p. 122°-4° C.

Replacement of palmitoyl chloride by acetyl chloride produces N,N-dioctadecyl-N',N'-bis(2-acetyloxyethyl)-1,3-propanediamine. Its hydrochloride salt prepared by standard methods melts at 103°-7° C.

Repetition of this procedure but using the appropriate acid chloride in place of palmitoyl chloride produces the following compounds:

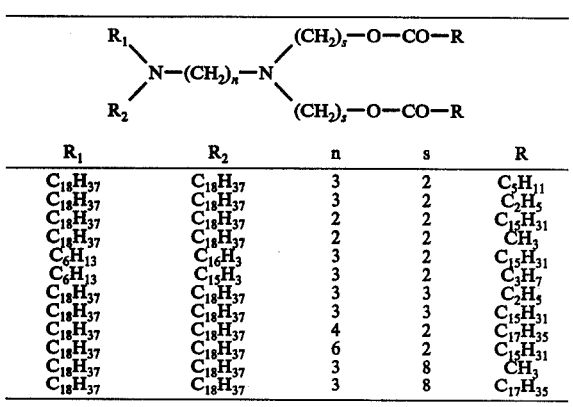

| $R_1$ | $R_2$ | n | s | R |
|---|---|---|---|---|
| $C_{18}H_{37}$ | $C_{18}H_{37}$ | 3 | 2 | $C_5H_{11}$ |
| $C_{18}H_{37}$ | $C_{18}H_{37}$ | 3 | 2 | $C_2H_5$ |
| $C_{18}H_{37}$ | $C_{18}H_{37}$ | 2 | 2 | $C_{15}H_{31}$ |
| $C_{18}H_{37}$ | $C_{18}H_{37}$ | 2 | 2 | $CH_3$ |
| $C_6H_{13}$ | $C_6H_{13}$ | 3 | 2 | $C_{15}H_{31}$ |
| $C_6H_{13}$ | $C_{15}H_{31}$ | 3 | 2 | $C_3H_7$ |
| $C_{18}H_{37}$ | $C_{18}H_{37}$ | 3 | 3 | $C_2H_5$ |
| $C_{18}H_{37}$ | $C_{18}H_{37}$ | 3 | 3 | $C_{15}H_{31}$ |
| $C_{18}H_{37}$ | $C_{18}H_{37}$ | 4 | 2 | $C_{17}H_{35}$ |
| $C_{18}H_{37}$ | $C_{18}H_{37}$ | 6 | 2 | $C_{15}H_{31}$ |
| $C_{18}H_{37}$ | $C_{18}H_{37}$ | 3 | 8 | $CH_3$ |
| $C_{18}H_{37}$ | $C_{18}H_{37}$ | 3 | 8 | $C_{17}H_{35}$ |

EXAMPLE XI

1,1-Dioctadecyl-3-{2-[Bis(2-Hydroxyethyl)Amino]Ethyl}Urea

A mixture of N,N-dioctadecylcarbamyl chloride (2.9 g.), N,N-bis-(2-hydroxyethyl)-1,2-ethanediamine (4.0 g.) and benzene (50 ml.) is refluxed and stirred for three hours. The mixture is then cooled, concentrated in vacuo and the residue taken up on chloroform (100 ml.). The chloroform solution is washed successively with water (2 × 50 ml.), aqueous sodium hydroxide (1 × 50 ml. of 1N) and water (2 × 50 ml.), then dried ($Na_2SO_4$). Removal of the chloroform in vacuo leaves the crude product as an oil (3.3 g.).

It is purified by chromatography on silica gel and elution with ethylacetate.

The hydrochloride salt is obtained by dissolving the purified product (0.75 g.) in ether (30 ml.) and bubbling in dry hydrogen chloride gas. Concentration of the ether provides the salt; 0.55 g., m.p. 152°-153° C.

The N,N-dioctadecylcarbamyl chloride is prepared by bubbling phosgene into a solution of N,N-dioctadecylamine (100 g.) in chloroform (1.2 liters) at room temperature for three hours. The mixture is stirred for two hours, then filtered. The filtrate is evaporated to provide the product (48 g.).

The following urea derivatives are similarly prepared but substituting N,N-bis(2-hydroxyethyl)-1,2-ethanediamine by the appropriate reactant: H―――NH―($CH_2$)$_n$―]$_m$$NR_3R_4$:

$$\begin{array}{c} C_{18}H_{37} \\ \diagdown \\ \phantom{xx} N-C\text{-}[NH-(CH_2)_n\text{-}]_mN \\ \diagup \\ C_{18}H_{37} \end{array} \begin{array}{c} R_3 \\ \diagdown \\ \\ \diagup \\ R_4 \end{array}$$

| $R_3$ | $R_4$ | m | n | Salt | M.P. (° C.) |
|---|---|---|---|---|---|
| $CH_2CH_2OH$ | $CH_2CH_2OH$ | 1 | 3 | — | 53-5 |
| $CH_3$ | $CH_3$ | 1 | 2 | HCl | 71-4 |
| $CH_2CH_2OH$ | $CH_2CH_2OH$ | 1 | 5 | HCl | 120-3 |
| H | $CH_2CH_2OH$ | 0 | — | — | 60-1 |
| $CH_2CH_2OH$ | $CH_2CH_2OH$ | 0 | — | — | 46-7 |
| H | $CH_2CH_2OCH_3$ | 0 | — | — | 44-5 |
| $CH_2CH_2OH$ | $CH_2CH_2OH$ | 1 | 2 | HCl | 152-3 |
| H | $CH_2CH_2COOH$ | 0 | — | — | 77-81 |
| H | H | 0 | — | — | 61-2 |
| ―$CH_2$―$CH_2$―O―$CH_2$―$CH_2$― | | 0 | — | — | 42-4 |

The compounds listed below are prepared in like manner from the appropriate reactants.

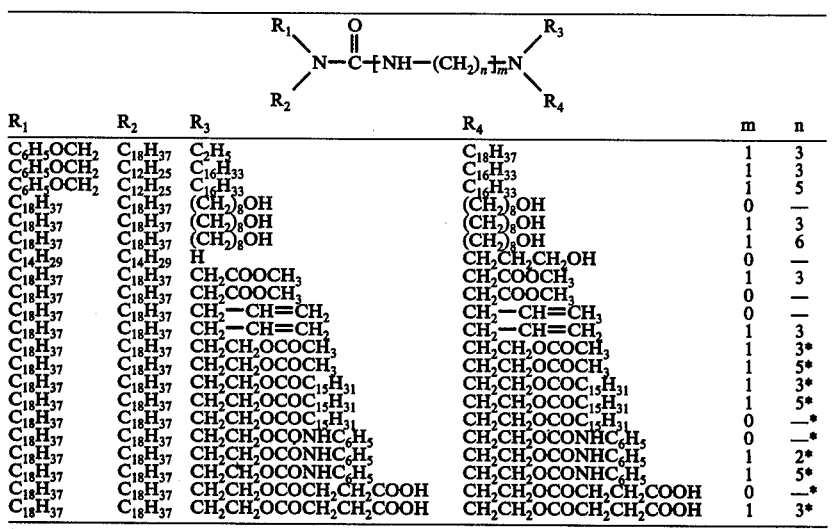

| $R_1$ | $R_2$ | $R_3$ | $R_4$ | m | n |
|---|---|---|---|---|---|
| $C_6H_5OCH_2$ | $C_{18}H_{37}$ | $C_2H_5$ | $C_{18}H_{37}$ | 1 | 3 |
| $C_6H_5OCH_2$ | $C_{12}H_{25}$ | $C_{16}H_{33}$ | $C_{16}H_{33}$ | 1 | 3 |
| $C_6H_5OCH_2$ | $C_{12}H_{25}$ | $C_{16}H_{33}$ | $C_{16}H_{33}$ | 1 | 5 |
| $C_{18}H_{37}$ | $C_{18}H_{37}$ | $(CH_2)_8OH$ | $(CH_2)_8OH$ | 0 | — |
| $C_{18}H_{37}$ | $C_{18}H_{37}$ | $(CH_2)_8OH$ | $(CH_2)_8OH$ | 1 | 3 |
| $C_{18}H_{37}$ | $C_{18}H_{37}$ | $(CH_2)_8OH$ | $(CH_2)_8OH$ | 1 | 6 |
| $C_{14}H_{29}$ | $C_{14}H_{29}$ | H | $CH_2CH_2CH_2OH$ | 0 | — |
| $C_{18}H_{37}$ | $C_{18}H_{37}$ | $CH_2COOCH_3$ | $CH_2COOCH_3$ | 1 | 3 |
| $C_{18}H_{37}$ | $C_{18}H_{37}$ | $CH_2COOCH_3$ | $CH_2COOCH_3$ | 0 | — |
| $C_{18}H_{37}$ | $C_{18}H_{37}$ | $CH_2\text{―}CH=CH_2$ | $CH_2\text{―}CH=CH_2$ | 0 | — |
| $C_{18}H_{37}$ | $C_{18}H_{37}$ | $CH_2\text{―}CH=CH_2$ | $CH_2\text{―}CH=CH_2$ | 1 | 3* |
| $C_{18}H_{37}$ | $C_{18}H_{37}$ | $CH_2CH_2OCOCH_3$ | $CH_2CH_2OCOCH_3$ | 1 | 3* |
| $C_{18}H_{37}$ | $C_{18}H_{37}$ | $CH_2CH_2OCOCH_3$ | $CH_2CH_2OCOCH_3$ | 1 | 5* |
| $C_{18}H_{37}$ | $C_{18}H_{37}$ | $CH_2CH_2OCOC_{15}H_{31}$ | $CH_2CH_2OCOC_{15}H_{31}$ | 1 | 3* |
| $C_{18}H_{37}$ | $C_{18}H_{37}$ | $CH_2CH_2OCOC_{15}H_{31}$ | $CH_2CH_2OCOC_{15}H_{31}$ | 1 | 5* |
| $C_{18}H_{37}$ | $C_{18}H_{37}$ | $CH_2CH_2OCOC_{15}H_{31}$ | $CH_2CH_2OCOC_{15}H_{31}$ | 0 | —* |
| $C_{18}H_{37}$ | $C_{18}H_{37}$ | $CH_2CH_2OCONHC_6H_5$ | $CH_2CH_2OCONHC_6H_5$ | 0 | —* |
| $C_{18}H_{37}$ | $C_{18}H_{37}$ | $CH_2CH_2OCONHC_6H_5$ | $CH_2CH_2OCONHC_6H_5$ | 1 | 2* |
| $C_{18}H_{37}$ | $C_{18}H_{37}$ | $CH_2CH_2OCONHC_6H_5$ | $CH_2CH_2OCONHC_6H_5$ | 1 | 5* |
| $C_{18}H_{37}$ | $C_{18}H_{37}$ | $CH_2CH_2OCOCH_2CH_2COOH$ | $CH_2CH_2OCOCH_2CH_2COOH$ | 0 | —* |
| $C_{18}H_{37}$ | $C_{18}H_{37}$ | $CH_2CH_2OCOCH_2CH_2COOH$ | $CH_2CH_2OCOCH_2CH_2COOH$ | 1 | 3* |

*Prepared from the corresponding hydroxyalkyl compounds of this example by the reactions of Examples VIII - X.

EXAMPLE XII

N-(2-Hydroxyethyl)Octadecylamine

A mixture of octadecyl bromide (6.66 g., 0.02 mole), ethanolamine (0.61 g., 0.01 mole), potassium carbonate (4.14 g., 0.03 mole) and benzyl alcohol (4 ml.) is heated overnight at 135°–145° C. The mixture is cooled, treated with ethylacetate (50 ml.) and 10 percent aqueous sodium hydroxide (10 ml.). The ethylacetate layer is separated, washed with water, and dried ($Na_2SO_4$). Removal of the organic solvents under reduced pressure gives an oily residue which solidifies upon cooling. It is purified by chromatography on alumina with chloroform as eluant. Its hydrobromide salt is prepared by adding hydrogen bromide to an ethanol solution of the base. It melts at 172°–173° C.

The compounds tabulated below are prepared from the appropriate reactants A-Y-Br and H—$NR_5R_6$ by the above procedure:

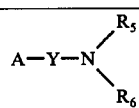

| Y | A | $R_5$ | $R_6$ | Salt | M.P. (° C.) |
|---|---|---|---|---|---|
| —$(CH_2)_3$— | OH | $C_{18}H_{37}$ | $C_{18}H_{37}$ | HBr | 78–82 |
| —$(CH_2)_3$— | OH | $C_{18}H_{37}$ | $C_{18}H_{37}$ | — | 37–40 |
| —$(CH_2)_3$— | OH | $C_{18}H_{37}$ | $C_{18}H_{37}$ | — | 38–42 |
| —$(CH_2)_6$— | OH | $C_{18}H_{37}$ | $C_{18}H_{37}$ | — | (a wax) |
| —$(CH_2)_2$— | $CN^{(a)}$ | $C_{18}H_{37}$ | $C_{18}H_{37}$ | — | 57–58 |
| —$(CH_2)_2$— | CN | $C_{18}H_{37}$ | $C_{18}H_{37}$ | HCl | 73–74 |
| —$(CH_2)_2$— | OH | $C_{18}H_{37}$ | $C_{18}H_{37}$ | — | 35–37 |
| —$(CH_2)_2$— | OH | $C_{18}H_{37}$ | $C_{18}H_{37}$ | HBr | 74–78 |
| —$(CH_2)_2$— | $OCOCH_3^{(b)}$ | $C_{18}H_{37}$ | $C_{18}H_{37}$ | — | 32–35 |
| —$(CH_2)_2$— | $OC_2H_5$ | $C_{18}H_{37}$ | $C_{18}H_{37}$ | — | <30 |
| —$(CH_2)_3$— | $OCONHC_6H_5^{(b)}$ | $C_{18}H_{37}$ | $C_{18}H_{37}$ | — | 197–198 |
| —$(CH_2)_3$— | Br | $C_{18}H_{37}$ | $C_{18}H_{37}$ | — | 116–119 |
| —$(CH_2)_3$— | CHO | $C_{18}H_{37}$ | $C_{18}H_{37}$ | — | 52–52.5 |
| —$(CH_2)_3$— | $OCOCH_3^{(b)}$ | $C_{18}H_{37}$ | $C_{18}H_{37}$ | — | (a wax) |
| —$(CH_2)_2$— | $CN^{(a)}$ | $C_{18}H_{37}$ | H | — | 84–85 |

$^{(a)}$Prepared by cyanoethylation procedure of Vogel et al., J.C.S. 514–49 (1952).
$^{(b)}$The acyl and carbamyl derivatives are prepared by the standard methods described by Shriner et al., "The Systematic Identification of Organic Compounds," John Wiley & Sons, Inc., New York, 1956, pp. 212 and 211, respectively.

EXAMPLE XIII

The procedure of Example XI is followed using the appropriate reactants A—Y—$NHR_6 R_5$—Br to give the compounds listed below:

$$A-Y-N\begin{matrix}R_5\\\\R_6\end{matrix}$$

| Y | A | $R_5$ | $R_6$ |
|---|---|---|---|
| —$(CH_2)_3$— | CN | $CH_3$ | $C_{18}H_{37}$ |
| —$(CH_2)_3$— | CN | $C_6H_{13}$ | $C_{16}H_{33}$ |
| —$(CH_2)_2$— | OH | $C_2H_5$ | $C_{12}H_{25}$ |
| —$(CH_2)_6$— | OH | $C_2H_5$ | $C_{12}H_{25}$ |
| —$(CH_2)_6$— | Br | $C_{12}H_{25}$ | $C_{12}H_{25}$ |
| —$(CH_2)_5$— | Br | $C_{14}H_{29}$ | $C_{14}H_{29}$ |
| —$(CH_2)_5$— | $OCOCH_3$ | $C_{12}H_{25}$ | $C_{12}H_{25}$ |
| —$(CH_2)_5$— | $OCOC_3H_7$ | $C_{18}H_{37}$ | $C_{18}H_{37}$ |
| —$(CH_2)_3$— | $OCH_3$ | $C_{16}H_{33}$ | $C_{16}H_{33}$ |
| —$(CH_2)_3$— | $OCH_3$ | $C_{12}H_{25}$ | $C_{12}H_{25}$ |
| —$(CH_2)_4$— | $OC_4H_9$ | $C_{10}H_{21}$ | $C_{10}H_{21}$ |
| —$(CH_2)_3$— | $OCONHC_6H_5$ | H | $C_{16}H_{33}$ |
| —$(CH_2)_2$— | $OCOCH_2CH_2COOH$ | $C_{14}H_{29}$ | $C_{14}H_{29}$ |
| —$(CH_2)_2$— | $OCOCH_2CH_2COOH$ | $C_{18}H_{37}$ | $C_{18}H_{37}$ |
| —$(CH_2)_6$— | $OCOCH_2CH_2COOH$ | $C_{18}H_{37}$ | $C_{18}H_{37}$ |
| —$(CH_2)_3$— | $OCOC_2H_5$ | $C_{18}H_{37}$ | $C_{18}H_{37}$ |

-continued $$A-Y-N\begin{matrix}R_5\\\\R_6\end{matrix}$$

| Y | A | $R_5$ | $R_6$ |
|---|---|---|---|
| —$(CH_2)_4$— | $OCOC_2H_5$ | $C_{18}H_{37}$ | $C_{18}H_{37}$ |
| —$(CH_2)_2$— | $OCOC_2H_5$ | $C_{18}H_{37}$ | $C_{18}H_{37}$ |
| —$(CH_2)_3$— | $OCOC_{15}H_{31}$ | $C_{18}H_{37}$ | $C_{18}H_{37}$ |
| —$(CH_2)_3$— | $OCOC_{15}H_{31}$ | $C_{12}H_{25}$ | $C_{12}H_{25}$ |
| —$(CH_2)_2$— | $COOCH_3$ | $C_{18}H_{37}$ | $C_{18}H_{37}$ |
| —$(CH_2)_3$— | $COOC_{15}H_{31}$ | $C_{18}H_{37}$ | $C_{18}H_{37}$ |
| —$(CH_2)_3$— | $COOC_{15}H_{31}$ | $C_{16}H_{33}$ | $C_{16}H_{33}$ |
| —$(CH_2)_5$— | Cl | $C_2H_5$ | $C_{12}H_{25}$ |
| —$(CH_2)_5$— | CN | $C_2H_5$ | $C_{12}H_{25}$ |
| —$(CH_2)_5$— | $COOC_2H_5$ | $C_{12}H_{25}$ | $C_{12}H_{25}$ |
| —$(CH_2)_4$— | $COOC_2H_5$ | $C_{16}H_{33}$ | $C_{16}H_{33}$ |
| —$(CH_2)_4$— | $COOC_9H_{19}$ | $C_{16}H_{33}$ | $C_{16}H_{33}$ |
| —$(CH_2)_8$— | OH | $C_{18}H_{37}$ | $C_{18}H_{37}$ |
| —$(CH_2)_8$— | Cl | $C_{18}H_{37}$ | $C_{18}H_{37}$ |
| —$(CH_2)_8$— | CN | $C_{18}H_{37}$ | $C_{18}H_{37}$ |
| —$(CH_2)_8$— | $OC_2H_5$ | $C_{18}H_{37}$ | $C_{18}H_{37}$ |

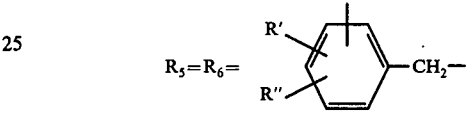

| A | Y | $R^o$ | $R'$ | $R''$ |
|---|---|---|---|---|
| HO | —$(CH_2)_2$— | 4-$OC_{18}H_{37}$ | H | H |
| HO | —$(CH_2)_3$— | 4-$OC_{18}H_{17}$ | H | H |
| HO | —$(CH_2)_3$— | 3-$OC_6H_{13}$ | 4-$OC_6H_{13}$ | H |
| HO | —$(CH_2)_6$— | 3-$OC_6H_{13}$ | 4-$OC_6H_{13}$ | H |
| HO | —$(CH_2)_2$— | 2-$OCH_3$ | 4-$OC_{12}H_{25}$ | 5-$OCH_3$ |
| HO | —$(CH_2)_4$— | 2-$OC_6H_{13}$ | 3-$OC_2H_5$ | H |
| HO | —$(CH_2)_3$— | 3-$OC_{12}H_{25}$ | 4-$OC_2H_5$ | H |
| HO | —$(CH_2)_2$— | 4-$OC_{18}H_{37}$ | 2-$CH_3$ | 6-$CH_3$ |
| HO | —$(CH_2)_8$— | 4-$OC_8H_{17}$ | H | H |
| CN | —$(CH_2)_2$— | 4-$OC_{18}H_{37}$ | H | H |
| CN | —$(CH_2)_2$— | 2-$OCH_3$ | 4-$OC_{12}H_{25}$ | 5-$OCH_3$ |
| CN | —$(CH_2)_2$— | 2-$OC_6H_{13}$ | 3-$OC_2H_5$ | H |
| CN | —$(CH_2)_5$— | 4-$OC_8H_{17}$ | H | H |
| Cl | —$(CH_2)_3$— | 3-$OC_6H_{13}$ | 4-$OC_6H_{13}$ | H |
| Cl | —$(CH_2)_6$— | 3-$OC_6H_{13}$ | 4-$OC_6H_{13}$ | H |
| Cl | —$(CH_2)_3$— | 4-$OC_{14}H_{29}$ | H | H |
| Br | —$(CH_2)_3$— | 4-$OC_{14}H_{29}$ | H | H |
| Br | —$(CH_2)_3$— | 2-$OCH_3$ | 4-$OC_{12}H_{25}$ | 5-$OCH_3$ |
| Cl | —$(CH_2)_3$— | 4-$OC_{18}H_{37}$ | 2-$CH_3$ | 6-$CH_3$ |
| $OCOCH_3$ | —$(CH_2)_2$— | 4-$OC_{18}H_{37}$ | H | H |
| $OCOC_3H_7$ | —$(CH_2)_3$— | 4-$OC_{18}H_{37}$ | H | H |
| $OCOC_{15}H_{31}$ | —$(CH_2)_3$— | 4-$OC_{18}H_{37}$ | 2-$CH_3$ | 6-$CH_3$ |
| $OCO_{10}H_{21}$ | —$(CH_2)_3$— | 2-$OCH_3$ | 4-$OC_{12}H_{25}$ | 5-$OCH_3$ |
| $OCOC_3H_7$ | —$(CH_2)_4$— | 2-$OC_6H_{13}$ | 3-$OC_2H_5$ | H |
| $OCOC_4H_9$ | —$(CH_2)_3$— | 3-$OC_6H_{13}$ | 4-$OC_6H_{13}$ | H |
| $OCOC_4H_9$ | —$(CH_2)_6$— | 3-$OC_6H_{13}$ | 4-$OC_6H_{13}$ | H |
| $OCOC_{17}H_{35}$ | —$(CH_2)_8$— | 4-$OC_8H_{17}$ | H | H |
| $COOC_2H_5$ | —$(CH_2)_2$— | 4-$OC_{18}H_{37}$ | H | H |
| $COOCH_3$ | —$(CH_2)_3$ | 3-$OC_6H_{13}$ | 4-$OC_6H_{13}$ | H |
| $COOCH_3$ | —$(CH_2)_6$— | 3-$OC_6H_{13}$ | 4-$OC_6H_{13}$ | H |
| $COOC_2H_5$ | —$(CH_2)_4$— | 2-$OCH_3$ | 4-$OC_{12}H_{25}$ | 5-$OCH_3$ |
| $COOC_2H_5$ | —$(CH_2)_3$— | 4-$OC_{18}H_{37}$ | 2-$CH_3$ | 6-$CH_3$ |
| $OCH_3$ | —$(CH_2)_3$— | 4-$OC_{18}H_{37}$ | 2-$CH_3$ | 6-$CH_3$ |
| $OCH_3$ | —$(CH_2)_3$— | 4-$OC_{18}H_{37}$ | H | H |
| $OCH_3$ | —$(CH_2)_3$— | 4-$OC_{18}H_{37}$ | H | H |
| $OC_6H_{13}$ | —$(CH_2)_3$— | 4-$OC_{18}H_{37}$ | H | H |
| $OCH_3$ | —$(CH_2)_3$— | 3-$OC_6H_{13}$ | 4-$OC_6H_{13}$ | H |
| $OC_{10}H_{21}$ | —$(CH_2)_3$— | 3-$OC_6H_{13}$ | 4-$OC_6H_{13}$ | H |
| $OC_{17}H_{35}$ | —$(CH_2)_3$— | 3-$OC_6H_{13}$ | 4-$OC_6H_{13}$ | H |
| O-n-$C_4H_9$ | —$(CH_2)_3$— | 2-$OCH_3$ | 4-$OC_{12}H_{25}$ | 5-$OCH_3$ |
| $OCONHC_6H_5$ | —$(CH_2)_2$— | 4-$OC_{18}H_{37}$ | H | H |
| $OCONHC_6H_5$ | —$(CH_2)_3$— | 3-$OC_6H_{13}$ | 4-$OC_6H_{13}$ | H |
| $OCONHC_6H_5$ | —$(CH_2)_6$— | 3-$OC_6H_{13}$ | 4-$OC_6H_{13}$ | H |
| $OCONHC_6H_5$ | —$(CH_2)_4$— | 2-$OCH_3$ | 4-$OC_{12}H_{25}$ | 5-$OCH_3$ |

EXAMPLE XIV

N,N-Dioctadecylsuccinamate

Dioctadecylamine (5.21 g., 0.01 mole) and succinic anhydride (0.50 g., 0.005 mole) are heated overnight at 105° C. on an oil bath. The mixture is poured over ice and the solid which forms separated by filtration; 4.9 g.; m.p. 57°–62° C. It is dissolved in chloroform (50 ml.) and the solution extracted with 6N hydrochloric acid (3 × 50 ml.). (The solid which formed at the interface is removed by filtration).

The chloroform phase is separated, washed with saturated aqueous sodium carbonate (3 × 50 ml.) and the emulsion which forms allowed to separate overnight. The chloroform layer is separated, dried ($Na_2SO_4$) and concentrated in vacuo to an oil. Trituration of the oil with acetone produces a brown solid; 2.03 g; m.p. 52°–58° C. Recrystallization from ethyl acetate raises the melting point to 77°–81° C.

The following compounds are made from appropriate reactants (anhydrides and amines) by this procedure:

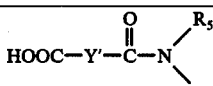

| Y' | $R_5$ | $R_6$ |
|---|---|---|
| $CH_2CH_2$ | $C_{16}H_{33}$ | $C_{16}H_{33}$ |
| $CH_2CH_2$ | $C_{16}H_{33}$ | $C_{16}H_{33}$ |
| $CH_2CH_2$ | $CH_3$ | $C_{18}H_{37}$ |
| $(CH_2)_3$ | $C_{18}H_{37}$ | $C_{18}H_{37}$ |
| $(CH_2)_3$ | $C_{18}H_{37}$ | $C_{12}H_{25}$ |
| $(CH_2)_3$ | $C_{12}H_{25}$ | H |
| $(CH_2)_3$ | $C_{12}H_{25}$ | $C_{12}H_{25}$ |
| $CH_2CH_2$ | H | $C_{12}H_{25}$ |
| $CH_2CH_2$ | H | $C_{16}H_{33}$ |
| $(CH_2)_3$ | H | $C_{20}H_{41}$ |

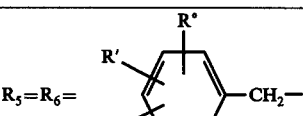

| Y' | R° | R' | R'' |
|---|---|---|---|
| $CH_2CH_2$ | 4-$OC_{18}H_{37}$ | H | H |
| $(CH_2)_3$ | 4-$OC_{18}H_{37}$ | H | H |
| $(CH_2)_3$ | 3-$OC_6H_{13}$ | 4-$OC_6H_{13}$ | H |
| $CH_2CH_2$ | 3-$OC_6H_{13}$ | 4-$OC_6H_{13}$ | H |
| $CH_2CH_2$ | 3,4-$O$-$CH_2$ | O | H |
| $CH_2CH_2$ | 4,5-$O$-$CH_2$ | O | 2-$C_3H_7$ |
| $CH_2CH_2$ | 2-$OCH_3$ | 4-$OC_{12}H_{25}$ | 5-$OCH_3$ |
| $(CH_2)_3$ | 3,4 - O - $CH_2$ | O | H |
| $(CH_2)_3$ | 4-$OC_8H_{17}$ | H | H |
| $(CH_2)_3$ | 4-$OC_{18}H_{37}$ | 2-$CH_3$ | 6-$CH_3$ |
| $CH_2CH_2$ | 4-$OC_{18}H_{37}$ | 2-$CH_3$ | 6-$CH_3$ |

EXAMPLE XV

N-(3-Dodecyloxypropyl)Diethanolamine and N-(3-Dodecyloxypropyl)Monoethanolamine A mixture of bromoethanol (2.50 g., 0.05 mole), 3-dodecyloxy-1-propylamine (2.43 g., 0.01 mole) and ethanol (20 ml.) is heated at reflux overnight. The solvent is removed by evaporation, the residue slurried in hot water (20 ml.) and made strongly alkaline with potassium hydroxide. The basic mixture is extracted with ether (3 × 50 ml.), the ethereal extracts dried ($MgSO_4$) and evaporated. The crude product mixture is purified by chromatography on alumina. Using ether as eluant removes the least polar impurity; elution with methanol removes the diethanolamine first, then the monoethanolamine derivative.

These two products appear as blue and yellow spots, respectively, when subjected to thin layer chromatography on a silica plate with methanol as eluant and iodoplatinic spray as developer.

The monoethanolamine derivatives boils at 160°–166° C. at 0.3 mm. mercury.

The following compounds are prepared in like manner from appropriate reactants: $A'$—O—$(CH_2)_n$—$NH_2$ and Br—$R_5$ $$A'-O-(CH_2)_n-N\begin{array}{c}R_5\\R_6\end{array} \quad (R_6 = H \text{ or } R_5)$$

| A' | n | $R_5$ | $R_6$ | Salt | M.P. (° C.) |
|---|---|---|---|---|---|
| $C_{12}H_{25}$ | 2 | $CH_3$ | $CH_3$ | $CH_3I$ | 165-7 |
| $C_{18}H_{37}$ | 3 | $CH_3$ | H | HI | 210-1 |
| $C_{18}H_{37}$ | 3 | $CH_2CH_2OH$ | H | HBr | |

EXAMPLE XVI

N-(3-Dodecylthiopropyl)Diethanolamine

A mixture of 3-octadecylthiopropyl chloride (3.53 g., 0.01 mole), diethanolamine (2.1 g., 0.02 mole) and benzyl alcohol (5 ml.) is heated under reflux for one-half hour, then treated with an ethanolic solution of sodium hydroxide (0.4 g., 0.01 mole) and refluxed for five more minutes. The mixture is cooled, filtered, and the ethanol removed by evaporation. The benzyl alcohol is then removed by distillation in vacuo and the residue chromatographed on silica using first ether then methanol as eluants. The desired product is contained in the methanol eluate. It is isolated by evaporation of the solvent, m.p. 53°–54° C. Its hydrochloride salt melts at 65°–66° C.

In like manner, the following compounds are prepared from the appropriate reactants: $A'$—S—$(CH_2)_n$—Cl and H—$NR_5R_6$ $$A'-S-(CH_2)_n-N\begin{array}{c}R_5\\R_6\end{array}$$

| A' | n | $R_5$ | $R_6$ | Salt | M.P. (° C.) |
|---|---|---|---|---|---|
| $C_{18}H_{37}$ | 3 | $CH_2CH_2OH$ | H | — | |
| $C_{18}H_{37}$ | 3 | $CH_2CH_2OC_2H_5$ | H | — | 155-7 |
| $C_{16}H_{33}$ | 3 | $CH_2CH_2OH$ | H | — | |
| $C_{16}H_{33}$ | 3 | $CH_2CH_2OH$ | $CH_2CH_2OH$ | HCl | 129-30 |
| $C_{14}H_{29}$ | 3 | $CH_2CH_2OH$ | $CH_2CH_2OH$ | — | 30-1 |
| $C_{14}H_{29}$ | 3 | $CH_2CH_2OH$ | $CH_2CH_2OH$ | HCl | 72 (dec.) |
| $C_{16}H_{33}$ | 2 | $C_2H_5$ | $C_2H_5$ | — | 175-8 (0.3 mm.) |
| $C_{18}H_{37}$ | 2 | $C_2H_5$ | $C_2H_5$ | — | 170-4 (0.2 mm.) |
| $C_{18}H_{37}$ | 2 | $C_2H_5$ | $C_2H_5$ | HCl | 102-4 |
| $C_{18}H_{37}$ | 2 | $(CH_2)_3N(C_2H_5)_2$ | H | 2HCl | |

EXAMPLE XVII

Following the procedures of Examples XV and XVI the compounds listed below are prepared from appropriate reactants:

| | | | | | | | |
|---|---|---|---|---|---|---|---|
| \multicolumn{8}{c}{$A-(CH_2)_n-N\begin{matrix}R_5\\R_6\end{matrix}$} |
| A | n | $R_5$ | $R_6$ | A | n | $R_5$ | $R_6$ |
| $CH_3O$ | 2 | $C_{18}H_{37}$ | $C_{18}H_{37}$ | $C_{12}H_{25}O$ | 3 | $C_{18}H_{37}$ | H |
| $C_{12}H_{25}O$ | 3 | $C_{18}H_{37}$ | $C_{18}H_{37}$ | $C_6H_5S$ | 3 | $C_{10}H_{21}$ | $C_{10}H_{21}$ |
| $C_2H_5O$ | 6 | $C_{18}H_{37}$ | $C_{18}H_{37}$ | $C_{18}H_{37}S$ | 3 | $C_{18}H_{37}$ | H |
| $C_{18}H_{37}O$ | 3 | $C_{18}H_{37}$ | $C_{18}H_{37}$ | $C_{18}H_{37}S$ | 3 | $C_{18}H_{37}$ | $C_{18}H_{37}$ |
| $C_6H_{13}O$ | 3 | $C_{16}H_{33}$ | $C_{16}H_{33}$ | $C_{16}H_{33}S$ | 2 | $C_{12}H_{25}$ | $C_{12}H_{25}$ |
| | | | | $C_{16}H_{33}S$ | 2 | H | $C_{12}H_{25}$ |
| | | | | $CH_3S$ | 6 | $C_{18}H_{37}$ | $C_{18}H_{37}$ |

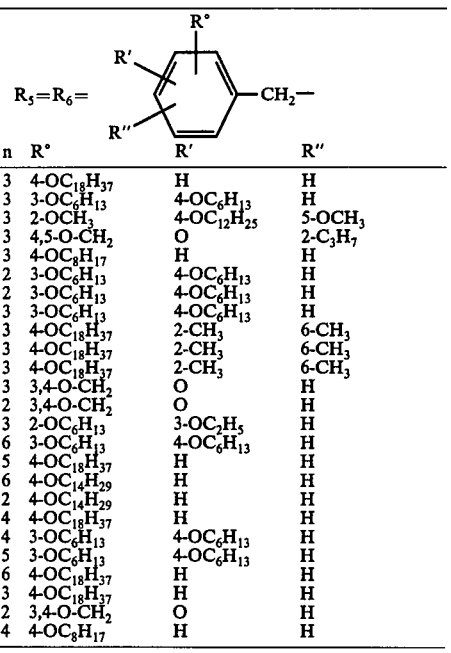

| A | n | R° | R' | R'' |
|---|---|---|---|---|
| $C_{18}H_{37}O$ | 3 | $4-OC_{18}H_{37}$ | H | H |
| $C_{18}H_{37}O$ | 3 | $3-OC_6H_{13}$ | $4-OC_6H_{13}$ | H |
| $C_{18}H_{37}O$ | 3 | $2-OCH_3$ | $4-OC_{12}H_{25}$ | $5-OCH_3$ |
| $C_{18}H_{37}O$ | 3 | $4,5-O-CH_2$ | O | $2-C_3H_7$ |
| $C_{18}H_{37}O$ | 3 | $4-OC_8H_{17}$ | H | H |
| $C_{18}H_{37}O$ | 2 | $3-OC_6H_{13}$ | $4-OC_6H_{13}$ | H |
| $C_{16}H_{33}O$ | 2 | $3-OC_6H_{13}$ | $4-OC_6H_{13}$ | H |
| $C_{16}H_{33}O$ | 3 | $3-OC_6H_{13}$ | $4-OC_6H_{13}$ | H |
| $C_{16}H_{33}O$ | 3 | $4-OC_{18}H_{37}$ | $2-CH_3$ | $6-CH_3$ |
| $CH_3O$ | 3 | $4-OC_{18}H_{37}$ | $2-CH_3$ | $6-CH_3$ |
| $C_6H_{13}O$ | 3 | $4-OC_{18}H_{37}$ | $2-CH_3$ | $6-CH_3$ |
| $C_2H_5O$ | 3 | $3,4-O-CH_2$ | O | H |
| $CH_3O$ | 2 | $3,4-O-CH_2$ | O | H |
| $C_{10}H_{21}O$ | 3 | $2-OC_6H_{13}$ | $3-OC_2H_5$ | H |
| $CH_3O$ | 6 | $3-OC_6H_{13}$ | $4-OC_6H_{13}$ | H |
| $C_{10}H_{21}O$ | 5 | $4-OC_{18}H_{37}$ | H | H |
| $CH_3O$ | 6 | $4-OC_{14}H_{29}$ | H | H |
| $C_4H_9S$ | 2 | $4-OC_{14}H_{29}$ | H | H |
| $C_{12}H_{25}S$ | 4 | $4-OC_{18}H_{37}$ | H | H |
| $C_{12}H_{25}S$ | 4 | $3-OC_6H_{13}$ | $4-OC_6H_{13}$ | H |
| $C_{10}H_{21}S$ | 5 | $3-OC_6H_{13}$ | $4-OC_6H_{13}$ | H |
| $CH_3S$ | 6 | $4-OC_{18}H_{37}$ | H | H |
| $C_{18}H_{37}S$ | 3 | $4-OC_{18}H_{37}$ | H | H |
| $C_{18}H_{33}S$ | 2 | $3,4-O-CH_2$ | O | H |
| $C_{10}H_{21}S$ | 4 | $4-OC_8H_{17}$ | H | H |

EXAMPLE XVIII

N-(2-Dodecanoylthioethyl)Diethylamine

Decanoyl chloride (1.90 g., 0.01 mole) in ether (250 ml.) is added to a mixture of diethylaminoethanoethiol (1.33 g., 0.01 mole) and triethylamine (1.01 g., 0.01 mole) in ether (250 ml.) and the reaction mixture stirred overnight at room temperature. The white precipitate is filtered off and the filtrate evaporated in vacuo to provide the product.

In like manner, N-(2-dodecanoyloxyethyl)diethylamine is prepared from decanoyl chloride and diethylaminoethanol. It boils at 103°–106° C. at 0.05 mm. mercury.

The following compounds are likewise prepared from appropriate reactants by this procedure:

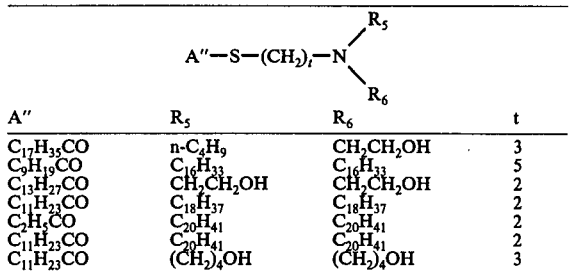

| A'' | $R_5$ | $R_6$ | t |
|---|---|---|---|
| $C_{17}H_{35}CO$ | $n-C_4H_9$ | $CH_2CH_2OH$ | 3 |
| $C_9H_{19}CO$ | $C_{16}H_{33}$ | $C_{16}H_{33}$ | 5 |
| $C_{13}H_{27}CO$ | $CH_2CH_2OH$ | $CH_2CH_2OH$ | 2 |
| $C_{11}H_{23}CO$ | $C_{18}H_{37}$ | $C_{18}H_{37}$ | 2 |
| $C_2H_5CO$ | $C_{20}H_{41}$ | $C_{20}H_{41}$ | 2 |
| $C_{11}H_{23}CO$ | $C_{20}H_{41}$ | $C_{20}H_{41}$ | 2 |
| $C_{11}H_{23}CO$ | $(CH_2)_4OH$ | $(CH_2)_4OH$ | 3 |

-continued

| | | | |
|---|---|---|---|
| \multicolumn{4}{c}{$A''-S-(CH_2)_t-N\begin{matrix}R_5\\R_6\end{matrix}$} |
| A'' | $R_5$ | $R_6$ | t |
| $C_{11}H_{23}CO$ | $C_{18}H_{37}$ | $C_{18}H_{37}$ | 6 |

| A'' | R° | R' | R'' | t |
|---|---|---|---|---|
| $CH_3CO$ | $4-OC_{18}H_{37}$ | $2-CH_3$ | $6-CH_3$ | 2 |
| $CH_3CO$ | $3-OC_6H_{13}$ | $4-OC_6H_{13}$ | H | 3 |
| $CH_3CO$ | $2-OCH_3$ | $4-OC_{12}H_{25}$ | $5-OCH_3$ | 3 |
| $CH_3CO$ | $4,5-O-CH_2$ | O | $2-C_3H_7$ | 6 |
| $C_3H_7CO$ | $4-OC_{18}H_{37}$ | $2-CH_3$ | $6-CH_3$ | 2 |
| $C_3H_7CO$ | $4-OC_{14}H_{29}$ | H | H | 3 |
| $C_3H_7CO$ | $3-OC_6H_{13}$ | $4-OC_6H_{13}$ | H | 6 |
| $C_{17}H_{35}CO$ | $3-OC_6H_{13}$ | $4-OC_6H_{13}$ | H | 6 |
| $C_{17}H_{35}CO$ | $3-OC_6H_{13}$ | $4-OC_6H_{13}$ | H | 3 |
| $C_{17}H_{35}CO$ | $4-OC_{14}H_{29}$ | H | H | 3 |
| $C_{17}H_{35}CO$ | $4,5-O-CH_2$ | O | $2-C_3H_7$ | 3 |
| $C_{12}H_{25}CO$ | $4-OC_{18}H_{37}$ | H | H | 3 |
| $C_7H_{15}CO$ | $4-OC_{18}H_{37}$ | H | H | 3 |
| $CH_3CO$ | $4-OC_{18}H_{37}$ | H | H | 3 |
| $C_{12}H_{25}CO$ | $4-OC_{18}H_{37}$ | H | H | 6 |
| $C_2H_5CO$ | $4-OC_{18}H_{37}$ | H | H | 6 |
| $C_5H_{11}CO$ | $3-OC_6H_{13}$ | $4-OC_6H_{13}$ | H | 6 |
| $C_{11}H_{23}CO$ | $3-OC_6H_{13}$ | $4-OC_6H_{13}$ | H | 6 |
| $CH_3CO$ | $3,4-O-CH_2$ | O | H | 6 |
| $C_9H_{19}CO$ | $3,4-O-CH_2$ | O | H | 6 |
| $C_7H_{15}CO$ | $4-OC_{18}H_{37}$ | $2-CH_3$ | $6-CH_3$ | 6 |
| $C_{13}H_{27}CO$ | $4-OC_{18}H_{37}$ | $2-CH_3$ | $6-CH_3$ | 3 |

EXAMPLE XIX

Ethyl 4-Dioctadecylaminobutyrate

A solution of dioctadecylamine (5.2 g., 0.01 mole), ethyl 4-bromobutyrate (1.95 g., 0.01 mole) and toluene (50 ml.) is heated at reflux for sixteen hours, then cooled and concentrated in vacuo to a semi-solid oil. The oil is triturated with ethylacetate, filtered, and the filtrate washed with water, then dried ($Na_2SO_4$). Removal of the solvent gives the product as an oil (3.7 g.).

It is purified by chromatography on silica gel and elution of the column first with benzene, then with benzene containing 20 percent ethylacetate. The residue obtained by evaporation of the benzene-20 percent ethylacetate solvent is taken up in ethylacetate and converted to the hydrochloride salt by bubbling dry hydrogen chloride through the solution. Concentration of the mixture in vacuo provides a crystalline material; m.p. 98°–101° C.

Substitution of ethyl 4-bromobutyrate by the appropriate lower alkyl ω-bromoalkanoate in the above procedure produces the following compounds:

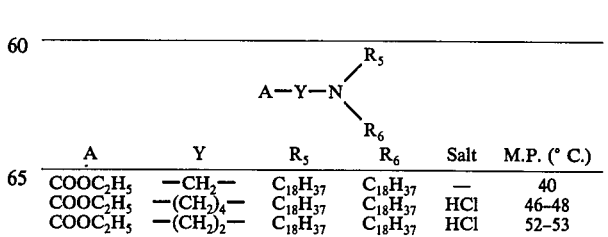

| A | Y | $R_5$ | $R_6$ | Salt | M.P. (° C.) |
|---|---|---|---|---|---|
| $COOC_2H_5$ | $-CH_2-$ | $C_{18}H_{37}$ | $C_{18}H_{37}$ | — | 40 |
| $COOC_2H_5$ | $-(CH_2)_4-$ | $C_{18}H_{37}$ | $C_{18}H_{37}$ | HCl | 46–48 |
| $COOC_2H_5$ | $-(CH_2)_2-$ | $C_{18}H_{37}$ | $C_{18}H_{37}$ | HCl | 52–53 |

EXAMPLE XX

1-(N,N-Dioctadecylcarbamyl)-4-Methylpiperazine

A mixture of 1-methylpiperazine (5 ml.), N,N-dioctadecylcarbamylchloride (5.0 g.) and benzene (50 ml.) is refluxed and stirred for three hours. The white precipitate of 1-methylpiperazine hydrochloride is removed by filtration and the filtrate concentrated in vacuo to a yellow oil (4.5 g.). The oil is then charged on a silica gel pad and eluted with benzene in 50 ml. fractions. Fractions 10–15 are combined, a large volume of methanol added and the white crystalline material which separates filtered and dried, m.p. 46°–47° C. (1.45 g.).

The following compounds are prepared from the appropriate reactants ($R_7R_8NCOCl$ and H—Z):

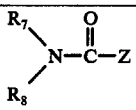

| $R_7$ | $R_8$ | Z |
|---|---|---|
| $C_{12}H_{25}$ | $C_{12}H_{25}$ | butylpiperazino |
| $C_{12}H_{25}$ | $C_{12}H_{25}$ | piperidino |
| $C_{12}H_{25}$ | $C_{12}H_{25}$ | morpholino |
| $C_{18}H_{37}$ | $CH_3$ | methylpiperazino |
| $C_{18}H_{37}$ | $CH_3$ | morpholino |
| $C_{18}H_{37}$ | $C_{18}H_{37}$ | hydroxyethylpiperazino |
| $C_{12}H_{25}$ | $C_{12}H_{25}$ | hydroxyethylpiperazino |
| $C_{18}H_{37}$ | $CH_3$ | hydroxyethylpiperazino |
| $C_{18}H_{37}$ | $C_{18}H_{37}$ | piperazino |
| $C_{12}H_{25}$ | $C_{12}H_{25}$ | piperazino |
| $C_{18}H_{37}$ | $CH_3$ | piperazino |

$R_7 = R_8 =$ (substituted benzyl with R°, R', R")—$CH_2—$

| R° | R' | R" | Z |
|---|---|---|---|
| 3-$OC_6H_{13}$ | 4-$OC_6H_{13}$ | H | piperidino |
| 3-$OC_6H_{13}$ | 4-$OC_6H_{13}$ | H | morpholino |
| 3-$OC_6H_{13}$ | 4-$OC_6H_{13}$ | H | piperazino |
| 4-$OC_{18}H_{37}$ | H | H | piperazino |
| 4-$OC_{18}H_{37}$ | H | H | morpholino |
| 4-$OC_{18}H_{37}$ | H | H | N-methylpiperazino |
| 4-$OC_{18}H_{37}$ | 2-$CH_3$ | 6-$CH_3$ | N-methylpiperazino |
| 4-$OC_{18}H_{37}$ | 2-$CH_3$ | 6-$CH_3$ | N-butylpiperazino |
| 3,4-O—$CH_2$—O— | | H | morpholino |
| 3,4-O—O—$CH_2$—O— | | H | n-(2-hydroxyethyl)-piperazino |
| 4-$OC_8H_{17}$ | H | H | N-(2-hydroxyethyl)-piperazino |
| 2-$OCH_3$ | 4-$OC_{12}H_{25}$ | 5-$OCH_3$ | N-(2-hydroxyethyl)-piperazino |
| 2-$OCH_3$ | 4-$OC_{12}H_{25}$ | 5-$OCH_3$ | piperidino |
| 2-$OCH_3$ | 4-$OC_{12}H_{25}$ | 5-$OCH_3$ | N-isopropylpiperazino |

EXAMPLE XXI

N,N-Dioctadecyl-N',N'-bis(2-Hydroxyethyl)-1,3-Propanediamine-N,N'-Dioxide

To a solution of N,N-dioctadecyl-N',N'-bis(2-hydroxyethyl)-1,3-propanediamine (3.34 g., 5 mM.) in chloroform (20 ml.) is added m-chloroperbenzoic acid (2.76 g., 12 mM. of 86 percent material) in chloroform (20 ml.) dropwise. The temperature is maintained at 28° C. throughout the addition and for 1.5 hours thereafter. The mixture is then diluted with chloroform (20 ml.) and the solution washed first with 1N aqueous sodium hydroxide then with brine. It is then dried ($Na_2SO_4$) and concentrated to an oil (2.5 g.).

The hydrochloride salt is prepared by the procedure of Example V; m.p. 89°–94° C., 114° C. (1.65 g. from 2.5 g. of oil).

Dissolution of the hydrochloride salt in chloroform and neutralization with aqueous sodium hydroxide regenerates the free base. It is recovered by drying the chloroform layer ($Na_2SO_4$) and evaporation of the solvent. Recrystallization from chloroform-ethylacetate provides the pure base; m.p. 95°–99° C.

The products of the preceding examples are converted to their N-oxide derivatives in like manner.

EXAMPLE XXII

N,N-Dioctadecyl-N',N'-bis(2-Hydroxyethyl)-1,3-Propanediamine N-Methonium Iodide Methyl iodide (568 mg., 4.0 ml.) is added all at once to a solution of N,N-dioctadecyl-N',N'-bis(2-hydroxyethyl)-1,3-propanediamine (1.334 g., 2.0 mM.) in methylene chloride (10 ml) which is cooled in an ice-bath. The mixture is stirred and allowed over a four-hour period to warm to room temperature, then stirred at room temperature overnight. The solid residue obtained by removal of the chloroform is recrystallized from ethylacetate; 1.35 g., m.p. 120°–122° C.

EXAMPLE XXIII

Repetition of the procedures of Example III-B and C, but using the appropriate alkanediamine and acid chloride reactants provides the following compounds:

$$R_1\!\!\diagdown\!\!N\!-\!(CH_2)_n\!-\!N\!\diagup\!\!\!\diagdown\!C(=O)\!-\!R_3 / R_4$$
(structure: $R_1R_2N$—$(CH_2)_n$—$N(R_4)$—C(=O)—$R_3$)

| $R_1$ | $R_2$ | n | $R_3$ | $R_4$ |
|---|---|---|---|---|
| $C_{18}H_{37}$ | $C_{18}H_{27}$ | 2 | H | H |
| $C_{18}H_{37}$ | $C_{18}H_{37}$ | 2 | $C_4H_9$ | H |
| $C_{18}H_{37}$ | $C_{18}H_{37}$ | 3 | H | $(CH_2)_4OH$ |
| $C_{18}H_{37}$ | $C_{18}H_{37}$ | 3 | $CH_3$ | $(CH_2)_4OH$ |
| $C_{18}H_{37}$ | $C_{18}H_{37}$ | 3 | H | $(CH_2)_5OH$ |
| $C_{18}H_{37}$ | $C_{18}H_{37}$ | 3 | $C_2H_5$ | $(CH_2)_5OH$ |
| $C_{18}H_{37}$ | $C_{18}H_{37}$ | 2 | H | $(CH_2)_5OH$ |
| $C_{18}H_{37}$ | $C_{18}H_{37}$ | 3 | H | n-$C_3H_7$ |

-continued

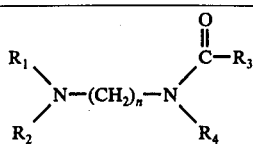

| R₁ | R₂ | n | R₃ | R₄ |
|---|---|---|---|---|
| $C_{18}H_{37}$ | $C_{18}H_{37}$ | 3 | H | n-$C_9H_{19}$ |
| $C_{18}H_{37}$ | $C_{18}H_{37}$ | 3 | $C_2H_5$ | n-$C_9H_{19}$ |

EXAMPLE XXIV

1-Dodecyl-4-(2-Hydroxyethyl)Piperazine

A solution of dodecylbromide (12.45 g., 0.05 mole) in ethanol (100 ml.) is added to a solution of 1-(2-hydroxyethyl)piperazine (6.5 g., 0.05 mole) in ethanol (100 ml.) and the mixture stirred and refluxed overnight. Evaporation of the solvent gives the hydrobromide salt which is recrystallized from acetone containing a small amount of ethanol. The white crystalline salt melts at 99°–103° C.

The free base is obtained by making an aqueous solution of the hydrobromide salt strongly alkaline with sodium hydroxide and extracting the base with chloroform. The chloroform solution is washed with water, dried ($Na_2SO_4$) and evaporated. The white solid which remains melts at 65°–67° C.

By means of the above procedure, the following compounds are prepared but using the appropriate alkyl bromide and 1-(hydroxyalkyl)piperazine reactants:

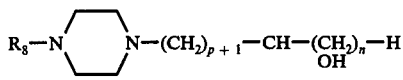

| $R_8$ | p + 1 | n | M.P. (degrees C.) |
|---|---|---|---|
| $C_{12}H_{25}$ | 3 | 0 | 55–7 |
| $C_{12}H_{25}$ | 3 | 0 | 95–8 (HBr salt) |
| $C_{18}H_{37}$ | 2 | 0 | 108–10 (HBr salt) |
| $C_{18}H_{37}$ | 3 | 0 | 111–12 (HBr salt) |
| $C_{12}H_{25}$ | 6 | 0 | |
| $C_{20}H_{41}$ | 3 | 0 | |
| $C_{18}H_{37}$ | 5 | 0 | |
| $C_{18}H_{37}$ | 2 | 1 | |
| $C_{12}H_{25}$ | 3 | 2 | |

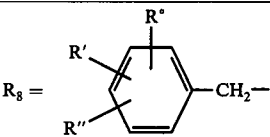

| R° | R′ | R″ | p + 1 | n |
|---|---|---|---|---|
| 3-$OC_6H_{13}$ | 4-$OC_6H_{13}$ | H | 2 | 0 |
| 3-$OC_6H_{13}$ | 4-$OC_6H_{13}$ | H | 3 | 0 |
| 3-$OC_6H_{13}$ | 4-$OC_6H_{13}$ | H | 6 | 0 |
| 4-$OC_{18}H_{37}$ | 2-$CH_3$ | 6-$CH_3$ | 3 | 0 |
| 4-$OC_{18}H_{37}$ | H | H | 3 | 0 |
| 4-$OC_{14}H_{29}$ | H | H | 5 | 0 |
| 3-$OCH_3$ | 4-$OC_{16}H_{33}$ | H | 2 | 0 |
| 4,5—O—$CH_2$—O— | | 2-$C_3H_7$ | 5 | 0 |
| 2-$OC_2H_5$ | 4-$OC_2H_5$ | 5-$C_6H_{13}$ | 5 | 0 |
| 3-$OC_6H_{13}$ | 4-$OC_6H_{13}$ | H | 2 | 1 |
| 4-$OC_{18}H_{37}$ | H | H | 2 | 1 |
| 2-$OCH_3$ | 4-$OC_{18}H_{37}$ | 5-$OCH_3$ | 2 | 1 |
| 2-$OC_{16}H_{33}$ | 4-$OC_{16}H_{33}$ | 5-$OC_{16}H_{33}$ | 2 | 1 |
| 2-$OC_{16}H_{33}$ | 4-$OC_{16}H_{33}$ | 5-$OC_{16}H_{33}$ | 2 | 2 |
| 3-$OC_6H_{13}$ | 4-$OC_6H_{13}$ | H | 2 | 2 |
| 3-$OC_6H_{13}$ | 4-$OC_6H_{13}$ | H | 3 | 2 |

-continued

| R° | R′ | R″ | p + 1 | n |
|---|---|---|---|---|
| 4-$OC_{18}H_{37}$ | H | H | 3 | 2 |

EXAMPLE XXV

N,N-Bis(3,4-Dihexoxybenzyl)-N′,N′-Bis(2-Hydroxyethyl)-1,3-Propanediamine

A mixture of 3,4-dihexoxybenzaldehyde (15.3 g., 0.05 M), sodium borohydride (1.85 g., 0.05 M) and ethanol (350 ml.) is stirred at room temperture for one hour and then concentrated in vacuo. The residue is dissolved in chloroform (500 ml.), the solution washed with water (4 × 100 ml.), dried ($Na_2SO_4$) and evaporated under reduced pressure to give 3,4-dihexoxybenzyl alcohol (15.0 g.) as a pale yellow oil.

Thionyl chloride (140 ml.) and 3,4-dihexoxybenzyl alcohol (14.0 g.) are combined and stirred at room temperature for ½ hour, at which time gas evolution ceases. The mixture is refluxed for one-half hour and then distilled to remove thionyl chloride (about 100 ml.). The residue is poured into ice-water (250 g. of each) and the aqueous solution extracted with chloroform (3 × 100 ml.). The chloroform extracts are combined, washed successively with saturated sodium bicarbonate solution (2 × 100 ml.) and water (3 × 100 ml.). It is then dried ($Na_2SO_4$) and concentrated to give 3,4-dihexoxybenzyl chloride as a brown oil (11.7 g.).

A mixture of N-(3-aminopropyl)diethanolamine (11.3 g., 7 mM), 3,4-dihexoxybenzyl chloride (4.8 g., 15 mM) and potassium carbonate (2.07 g., 15 mM) is stirred at room temperature for 16 hous and then at 130° C. for 2 hours. It is cooled, benzene (50 ml.) added and the mixture filtered. The benzene filtrate is charged onto a column and the column eluted with benzene (75 ml. fractions). The first eleven fractions collected are discarded. The column is then eluted with benzene containing 10% ethanol. The second and third fractions are collected, evaporated and the residue dissolved in methanol. The dihydrochloride salt is prepared by bubbling hydrogen chloride into the solution and then evaporating to a waxy solid (400 mg).

In like manner, the following, N,N-bis(alkoxybenzyl)-N′,N′-bis(2-hydroxyethyl)-1,3-propanediamines are prepared from appropriate reactants.

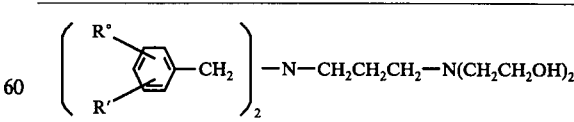

| R′ | R° | Base | Di-HCl M.P. (° C.) |
|---|---|---|---|
| H | 4-$C_{18}H_{37}O$ | — | >200 |
| H | 4-$C_{12}H_{25}O$ | oil | — |
| H | 4-$C_6H_{13}O$ | oil | — |
| 3-$C_{12}H_{25}O$ | 4-$C_{12}H_{25}O$ | — | 202–4 |

EXAMPLE XXVI

N,N-bis(3,4-Dihexoxybenzyl)-1,3-Propanediamine

Raney nickel (500 mg.), 3,4-dihexoxybenzaldehyde (6.12 g., 0.02 M) and ammonia (3.0 g., 0.177 M) in ethanol (100 ml.) are charged into a Paar shaker and hydrogenated at 40° C and an initial pressure of 51 psi. When approximately 20 psi drop in hydrogen pressure is observed, about 24 hours, the contents are removed and filtered. The filtrate is concentrated in vacuo to an amber oil which is dissolved in ethyl acetate (50 ml.). The solution is treated with ethyl acetate saturated with hydrogen chloride (100 ml.) and the resulting white hydrochloride salt collected; 3.7 g., m.p. 205°–206° C. The salt is then partitioned between chloroform (100 ml.) and saturated sodium bicarbonate solution (50 ml.). The chloroform phase is separated, washed with water (50 ml.), dried ($Na_2SO_4$) and concentrated to give 3,4-dihexoxybenzylamine as an oil; 3.2 g., 52.1% yield.

A solution of 3,4-dihexoxybenzylamine (2.0 g., 6.52 mM), 3,4-dihexoxybenzaldehyde (2.0 g., 6.52 mM), benzene (75 ml.) and p-toluenesulfonic acid (200 mg.) is refluxed with stirring in apparatus equipped with a Dean-Stark collctor for 16 hours. It is then cooled and concentrated in vacuo to an oil which crystallizes upon standing: 4.0 g. of the Schiff base.

The Schiff base is reduced by treatment with sodium borohydride (0.378 g.) in ethanol (50 ml. per 2.0 g. of Schiff base) at room temperature for 20 hours. The mixture is concentrated under reduced pressure to a solid which is taken up in methanol. Hydrogen chloride gas is bubbled into the solution, water (50 ml.) added and the salt filtered, washed with water and air dried. The dry salt is dissolved in warm methanol (75 ml.), saturated aqueous sodium bicarbonate (50 ml.) and water (50 ml.) added. The solid is filtered off, washed with water and air dried. It is then dissolved in chloroform (75 ml.), the solution washed with water (50 ml.), dried ($Na_2SO_4$) and concentrated to give bis(3,4-dihexoxybenzyl)amine as an oil; 1,4 g., 69.8% yield.

Acrylonitrile (15 ml.) and bis(3,4-dihexoxybenzyl)amine are refluxed together for 18 hours. The mixture is then cooled and concentrated in vacuo to an oil: 1.2 g.

The cyanoethyl derivative (1.2 g.), Raney nickel (500 mg.), ammonia (1.0 g.) and ethanol (75 ml.) are charged into a Paar shaker and hydrogenated at room temperature and an initial pressure of 50 psi. When uptake of hydrogen is complete, the contents are removed, filtered and concentrated to give the title product as an oil (1.02 g.).

The dihydrochloride salt is formed by dissolving the product in ether and bubbling hydrogen chloride into the solution. Removal of the ether under reduced pressure gives the salt.

Similarly, N,N-bis(3,4-diisopropoxybenzyl)-1,3-propanediamine is prepared by substituting 3,4-diisopropoxybenzaldehyde for 3,4-dihexoxybenzaldehyde. Its dihydrochloride salt melts at 65°–68° C.

EXAMPLE XXVII

The following N,N-bis (alkoxybenzyl)-α,ω-alkanediamine derivatives are prepared from appropriate reactants by the procedures of Examples, XXV, XXVI and XI.

| R° | R' | R'' | X | m | X' | $R_3$ | $R_4$ |
|---|---|---|---|---|---|---|---|
| 2-$OC_3H_7$ | 3-$OC_2H_5$ | H | — | 0 | —$CH_2CH_2$— | $CH_2CH_2OH$ | $CH_2CH_2OH$ |
| 3-$OCH_3$ | 4-$OC_{16}H_{33}$ | H | — | 0 | —$(CH_2)_3$— | $CH_2CH_2OH$ | $CH_2CH_2OH$ |
| 4-$OC_{16}H_{33}$ | H | H | — | 0 | —$(CH_2)_4$— | $CH_2CH_2OH$ | $CH_2CH_2OH$ |
| 3-$OC_{12}H_{25}$ | 4-$OC_{12}H_{25}$ | H | — | 0 | —$(CH_2)_3$— | $C_6H_{13}$ | $C_6H_{13}$ |
| 3-$OC_{12}H_{25}$ | 4-$OC_{12}H_{25}$ | H | — | 0 | —$(CH_2)_3$— | $C_{18}H_{37}$ | $C_{18}H_{37}$ |
| 3-$OC_6H_{13}$ | 4-$OC_6H_{13}$ | H | — | 0 | —$(CH_2)_6$— | $CH_2CH_2OH$ | $CH_2CH_2OH$ |
| 4-$OC_{18}H_{37}$ | H | H | — | 0 | —$(CH_2)_6OH$ | $(CH_2)_6OH$ | |
| 3-$OCH_3$ | 4-$OC_{16}H_{33}$ | H | — | 0 | —$(CH_2)_2$— | $C_{20}H_{41}$ | H |
| 2-$OC_2H_5$ | 4-$OC_2H_5$ | 5-$C_6H_{13}$ | — | 0 | —$(CH_2)_6$— | $C_{10}H_{21}$ | $C_{10}H_{21}$ |
| 4-$OC_8H_{17}$ | H | H | — | 0 | —$(CH_2)_3$— | $CH_2$—CH=$CH_2$ | $CH_2$—CH=$CH_2$ |
| 4-$OC_8H_{17}$ | H | H | —$CH_2CH_2$— | 1 | —$CH_2CH_2$— | $CH_2CH_2OH$ | $CH_2CH_2OH$ |
| 4-$OC_{18}H_{37}$ | H | H | —$(CH_2)_3$— | 1 | —$(CH_2)_3$— | $CH_2CH_2OH$ | $CH_2CH_2OH$ |
| 3-$OC_6H_{13}$ | 4-$OC_6H_{13}$ | H | —$(CH_2)_4$— | 1 | —$(CH_2)_4$— | $CH_2CH_2OH$ | $CH_2CH_2OH$ |
| 2-$OC_2H_5$ | 4-$OC_2H_5$ | 5-$C_2H_5$ | —$(CH_2)_3$— | 1 | —$(CH_2)_3$— | $C_{18}H_{37}$ | $C_{18}H_{37}$ |
| 2-$CH_3$ | 4-$OC_{18}H_{37}$ | 6-$CH_3$ | —$CH_2CH_2$— | 1 | —$(CH_2)_3$— | $(CH_2)_4OH$ | $(CH_2)_4OH$ |
| 2-$OCH_3$ | 4-$OC_{12}H_{25}$ | 6-$OCH_3$ | — | 0 | —$(CH_2)_3$— | $CH_2CHOHCH_2OH$ | $CH_2CHOHCH_2OH$ |
| 4-$OC_{12}H_{25}$ | 3-$OC_{12}H_{25}$ | H | — | 0 | —$(CH_2)_3$— | $CH_2CHOHCH_2OH$ | $CH_2CHOHCH_2OH$ |
| 4-$OC_{18}H_{37}$ | H | H | — | 0 | —$(CH_2)_3$— | H | $C_7H_{15}$ |
| 3-$OC_6H_{13}$ | 4-$OC_6H_{13}$ | H | —$(CH_2)_3$— | 1 | —$(CH_2)_3$— | $CH_2CHOHCH_3$ | $CH_2CHOHCH_3$ |
| 4-$OC_{18}H_{37}$ | 2-$CH_3$ | 6-$CH_3$ | — | 0 | —$(CH_2)_3$— | $CH_2COOCH_3$ | $CH_2COOCH_3$ |
| 4-$OC_{16}H_{33}$ | H | H | — | 0 | —$(CH_2)_2$— | $CH_2CH_2OC_{12}H_{25}$ | H |
| 2-O-i-$C_5H_{11}$ | 3-$OC_2H_5$ | H | —$(CH_2)_2$— | 1 | —$(CH_2)_2$— | $C_{18}H_{37}$ | $CH_2$—CH=$CH_2$ |
| 4-$OC_{18}H_{37}$ | H | H | —$(CH_2)_2$— | 1 | —$(CH_2)_2$— | $CH_2$—CH=$CH_2$ | $CH_2$—CH=$CH_2$ |
| 3-$OC_6H_{13}$ | 4-$OC_6H_{13}$ | H | — | 0 | —$(CH_2)_6$— | H | H |
| 4-$OC_{18}H_{37}$ | H | H | —$(CH_2)_2$— | 1 | —$(CH_2)_2$— | H | H |
| 2-$OC_6H_{13}$ | 4-$OC_6H_{13}$ | 5-$OC_6H_{13}$ | — | 0 | —$(CH_2)_3$— | $CH_2CH_2OH$ | $CH_2CH_2OH$ |
| 2-$OCH_3$ | 4-$OC_{18}H_{37}$ | 5-$OCH_3$ | — | 0 | —$(CH_2)_4$— | $C_8H_{17}$ | $C_8H_{17}$ |
| 2-$OCH_3$ | 4-$OC_{12}H_{25}$ | 5-$OCH_3$ | — | 0 | —$(CH_2)_3$— | H | H |
| 4-$OC_{14}H_{29}$ | H | H | — | 0 | —$(CH_2)_2$— | H | H |
| 2-$OC_6H_{13}$ | 3-$OC_2H_5$ | H | — | 0 | —$(CH_2)_3$— | H | H |
| 3-$OC_{12}H_{25}$ | 4-$OC_2H_5$ | H | — | 0 | —$(CH_2)_6$— | H | H |
| 4-$OC_{18}H_{37}$ | H | H | — | 0 | —$(CH_2)_3$— | H | H |
| 4-$OC_8H_{17}$ | H | H | — | 0 | —$(CH_2)_3$— | H | H |
| 4-$OC_{18}H_{37}$ | 2-$CH_3$ | 6-$CH_3$ | — | 0 | —$(CH_2)_3$— | $CH_2CH(OCH_3)_2$ | $CH_2$—CH=$CH_2$ |
| 3-$OC_6H_{13}$ | 4-$OC_6H_{13}$ | H | —CO— | 1 | —$(CH_2)_3$— | $CH_2CH_2OH$ | $CH_2CH_2OH$ |
| 4-$OC_{18}H_{37}$ | H | H | —CO— | 1 | —$(CH_2)_3$— | $(CH_2)_3OH$ | $(CH_2)_3OH$ |

-continued

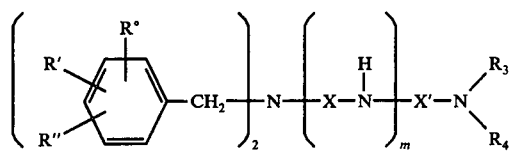

| R° | R' | R'' | X | m | X' | R₃ | R₄ |
|---|---|---|---|---|---|---|---|
| 3-OC₆H₁₃ | 4-OC₆H₁₃ | H | —CO— | 1 | —(CH₂)₅— | CH₂CH₂OH | CH₂CH₂OH |
| 4,5—O—CH₂—O— | | 2-C₃H₇ | —CO— | 1 | —(CH₂)₆— | (CH₂)₆OH | (CH₂)₆OH |
| 4-OC₁₄H₂₉ | H | H | —CO— | 1 | —(CH₂)₃— | CH₂CH₂OC₄H₉ | CH₂CH₂OC₄H₉ |
| 2-OC₆H₁₃ | 3-OC₂H₅ | H | —CO— | 1 | —(CH₂)₃— | CH₂COOCH₃ | CH₂COOCH₃ |
| 4-OC₈H₁₇ | H | H | —CO— | 1 | —(CH₂)₃— | CH₂—CH=CH₂ | CH₂—CH=CH₂ |
| 3-OCH₃ | 4-OC₆H₁₃ | 5-OCH₃ | —CO— | 1 | —(CH₂)₃— | CH₂COOC₃H₇ | CH₂COOC₃H₇ |
| 3-OC₁₂H₂₅ | 4-OC₁₂H₂₅ | H | —CO— | 1 | —(CH₂)₃— | (CH₂)₆OH | (CH₂)₆OH |
| 4-OC₈H₁₇ | H | H | —CO— | 1 | —(CH₂)₃— | CH₂CHOHCH₃ | CH₂CHOHCH₃ |
| 4-OC₈H₁₇ | H | H | —CO— | 1 | —(CH₂)₅— | (CH₂)₃OH | (CH₂)₃OH |
| 4-OC₈H₁₇ | H | H | —(CH₂)₃— | 1 | —CO— | CH₂CH₂OH | CH₂CH₂OH |
| 4-OC₈H₁₇ | H | H | —(CH₂)₃— | 1 | —CO— | C₆H₁₃ | C₆H₁₃ |
| 4-OC₁₄H₂₉ | H | H | —(CH₂)₂— | 1 | —CO— | CH₂CH₂OC₄H₉ | CH₂CH₂OC₄H₉ |
| 4-OC₁₄H₂₉ | H | H | —(CH₂)₂— | 1 | —CO— | CH₂—CH=CH₂ | CH₂—CH=CH₂ |
| 4-OC₁₈H₃₇ | H | H | —(CH₂)₃— | 1 | —CO— | CH₂COOCH₃ | CH₂COOCH₃ |
| 3-OC₁₂H₂₅ | 4-OC₂H₅ | H | —(CH₂)₆— | 1 | —CO— | CH₂CHOHCH₃ | CH₂CHOHCH₃ |
| 2-OC₆H₁₃ | 4-OC₆H₁₃ | 5-OC₆H₁₃ | —(CH₂)₃— | 1 | —CO— | (CH₂)₃OH | (CH₂)₃OH |
| 4-OC₁₈H₃₇ | H | H | — | 0 | —(CH₂)₂— | —CH₂CH₂—O— | CH₂CH₂— |
| 3-OC₆H₁₃ | 4-OC₆H₁₃ | H | — | 0 | —(CH₂)₂— | —CH₂CH₂—O— | CH₂CH₂— |
| 2-OCH₃ | 4-OC₁₂H₂₅ | 5-OCH₃ | — | 0 | —(CH₂)₂— | —CH₂CH₂—O— | CH₂CH₂— |
| 3-OC₆H₁₃ | 4-OC₆H₁₃ | H | — | 0 | 3 | —CH₂CH₂—O— | CH₂CH₂— |

The compounds of the above tabulation wherein $R_3$ and $R_4$ are hydroxyalkyl groups are converted to various derivatives by the procedures of Examples VIII – X. In this manner, the hydroxy groups are converted to -OCH₂CH₂COOH, -OCONCH₆H₅, —OCOCH₃ and —OCOC₁₅H₃₁.

EXAMPLE XXVIII

1-(Dioctadecylamino)methyl-4-[Bis-(2-Hydroxyethyl)Aminomethyl]Benzene

Dioctadecylamine (26.0 g., 0.05 M), α-bromo-p-tolunitrile (4.9 g., 0.025 M) and chloroform (500 ml.) are stirred at room temperature for 24 hours. The precipitate of dioctadecylamine hydrobromide is filtered off and the filtrate concentrated under reduced pressure. The residue is slurried in methanol, filtered, and evaporated to give 1-(dioctadecylamino)methyl-4-cyanobenzene (15.5 g., 97.5% yield).

The nitrile (15 g.), ethylene dichloride (200 ml.), methanol (50 ml.) and water (20 ml.) are combined and stirred at room temperature. Hydrogen chloride gas is bubbled into the mixture for three hours after which the yellow solution is refluxed for three hours. Methanol (50 ml.) and water (10 ml.) are added and hydrogen chloride bubbled into the mixture for one hour and refluxing continued for 14 hours. Methanol (10 ml.) and water (2 ml.) are added and hydrogen chloride bubbled in for 1 hour. The mixture is refluxed for four hours, cooled to room temperature and made alkaline by addition of saturated aqueous sodium bicarbonate solution. The ethylene dichloride phase is separated and the aqueous phase extracted with chloroform (2 × 100 ml.). The combined organic solutions are washed with water (100 ml.), dried ($Na_2SO_4$) and evaporated to give 1-(dioctadecylamino)methyl-4-carbomethoxy benzene (14.0 g., 73.6% yield).

A mixture of the thus produced ester (12.5 g., 18.7 mM), sodium dihydro bis-(2-methoxyethoxy)aluminate (11.0 g. of 70% reagent, 37.5 mM) and benzene (300 ml.) is stirred at reflux for 24 hours. The mixture is cooled, aqueous sodium hydroxide (50 ml. of 10% solution) added and the mixture thoroughly stirred. The benzene layer is separated, washed with water (100 ml.), dried ($Na_2SO_4$) and concentrated in vacuo to give the corresponding alcohol as a semi-solid (9.68 g., 80.8%).

Thionyl chloride (90 ml.) and the alcohol produced above (9.6 g.) are mixed and refluxed for one hour. The mixture is poured into ice-water (150 g. each of ice and water) and the precipitate which forms filtered off. It is dissolved in chloroform, the solution washed with saturated aqueous sodium carbonate until the wash had pH 8.0, and then with water (2 × 100 ml.). It is dried ($Na_2SO_4$) and concentrated to give 1-(dioctadecylamino)-methyl-4-chloromethyl benzene as an amber oil (8.3 g.). The residue is taken up in benzene and purified by chromatography on silica gel using benzene, benzene-10% ethanol, ethanol, and ethanol-methanol as successive eluents. The ethanol and ethanol-methanol eluates are combined and concentrated to give 4.58 g. of product.

A solution of the chloromethyl compound (2.1 g., 3.2 mM), diethanolamine (1.3 g., 12.8 mM), and ethanol (50 ml.) is stirred at reflux for 18 hours. It is cooled and concentrated in vacuo to an oil. The oil is taken up in chloroform (50 ml.), solution washed with water (2 × 50 ml.), dried with anhydrous sodium sulfate and evaporated to an oil, 2.3 g. It is purified by adsorption on a dry column of silica gel and elution with ethyl acetate. Concentration gives the title compound as a solid; 0.44 g., m.p. 49°–50° C.

In like manner, but using 2-amino-2-(hydroxymethyl)-1,3-propanediol in place of diethanolamine pro-cuces 1-(dioctadecylamino)methyl-4-[2-(2-hydroxymethyl)-1,3-dihydroxypropylamino methyl]benzene.

Repetition of this procedure but using didodecylamine in place of dioctadecylamine produces 1-(didodecylamino)methyl-4-[bis(2-hydroxyethyl)amino methyl]benzene. Its dihydrochloride salt prepared according to the procedure of Example XXV melts at 199°–204° C.

EXAMPLE XXIX

The following compounds are prepared from appropriate reactants by the procedure of Example XXVIII. The column headed "Isomer" refers to the phenylenedimethylene moiety substituents.

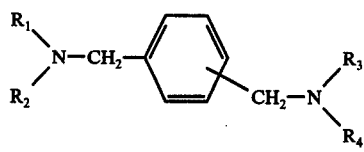

| Isomer | $R_1$ | $R_2$ | $R_3$ | $R_4$ |
|---|---|---|---|---|
| 1,3 | $C_{18}H_{37}$ | $C_{18}H_{37}$ | $CH_2CH_2OH$ | $CH_2CH_2OH$ |
| 1,2 | $C_{18}H_{37}$ | $C_{18}H_{37}$ | $CH_2CH_2OH$ | $CH_2CH_2OH$ |
| 1,3 | $C_{12}H_{25}$ | $C_{12}H_{25}$ | $CH_2CH_2OH$ | $CH_2CH_2OH$ |
| 1,2 | $C_{12}H_{25}$ | $C_{12}H_{25}$ | $CH_2CH_2OH$ | $CH_2CH_2OH$ |
| 1,4 | $C_{18}H_{37}$ | $C_{18}H_{37}$ | $(CH_2)_3OH$ | $(CH_2)_3OH$ |
| 1,4 | $CH_3$ | $C_{12}H_{25}$ | $C_2H_5$ | $C_2H_5$ |
| 1,3 | $C_{16}H_{33}$ | $C_{16}H_{33}$ | $C_6H_{13}$ | $C_6H_{13}$ |
| 1,2 | $C_{18}H_{37}$ | $C_{18}H_{37}$ | $CH_2CHOHCH_3$ | $CH_2CHOHCH_3$ |
| 1,4 | n-$C_4H_9$ | $C_{16}H_{33}$ | $(CH_2)_8OH$ | $(CH_2)_8OH$ |
| 1,4 | $C_{18}H_{37}$ | $C_{18}H_{37}$ | $CH_2-CH=CH_2$ | $CH_2-CH=CH_2$ |
| 1,3 | $C_2H_5$ | $C_{20}H_{41}$ | $CH_2-CH=CH_2$ | $CH_2CH_2OH$ |
| 1,3 | $C_2H_5$ | $C_{14}H_{29}$ | $C_{12}H_{25}$ | $C_{12}H_{25}$ |
| 1,4 | $C_{18}H_{37}$ | $C_{18}H_{37}$ | $CH_2CH(OCH_3)_2$ | $CH_2-CH=CH_2$ |
| 1,4 | $C_{18}H_{37}$ | $C_{18}H_{37}$ | H | $CH_2CHOHCH_2OH$ |
| 1,3 | $C_{18}H_{37}$ | $C_{18}H_{37}$ | H | n-$C_7H_{15}$ |
| 1,3 | $C_{16}H_{33}$ | $C_{16}H_{33}$ | H | $CH(CH_3)CH_2OOC_2H_5$ |
| 1,3 | $C_{18}H_{37}$ | $C_{18}H_{37}$ | $CH_2COOCH_3$ | $CH_2COOCH_3$ |
| 1,3 | $C_{12}H_{25}$ | $C_{12}H_{25}$ | $(CH_2)_2OCOCH_2CH_2COOH$ | $(CH_2)_2OCOCH_2CH_2COOH$* |
| 1,4 | $C_{18}H_{37}$ | $C_{18}H_{37}$ | $(CH_2)_2OCOCH_2CH_2COOH$ | $(CH_2)_2OCOCH_2CH_2COOH$ |
| 1,4 | n-$C_4H_9$ | $C_{16}H_{33}$ | $(CH_2)_8OCOCH_2CH_2COOH$ | $(CH_2)_8OCOCH_2CH_2COOH$ |
| 1,4 | $C_{18}H_{37}$ | $C_{18}H_{37}$ | $(CH_2)_2OCONHC_6H_5$ | $(CH_2)_2OCONHC_6H_5$ |
| 1,3 | $C_{12}H_{25}$ | $C_{12}H_{25}$ | $(CH_2)_2OCONHC_6H_5$ | $(CH_2)_2OCONHC_6H_5$ |
| 1,4 | n-$C_4H_9$ | $C_{16}H_{33}$ | $(CH_2)_8OCONHC_6H_5$ | $(CH_2)_8OCONHC_6H_5$ |
| 1,3 | $C_{12}H_{25}$ | $C_{12}H_{25}$ | $(CH_2)_2OCOCH_3$ | $(CH_2)_2OCOCH_3$ |
| 1,4 | $C_{18}H_{37}$ | $C_{18}H_{37}$ | $(CH_2)_2OCOCH_3$ | $(CH_2)_2OCOCH_3$ |
| 1,4 | $C_{18}H_{37}$ | $C_{18}H_{37}$ | $(CH_2)_2OCOC_{17}H_{35}$ | $(CH_2)_2OCOC_{17}H_{35}$ |
| 1,3 | $C_{12}H_{25}$ | $C_{12}H_{25}$ | $(CH_2)_2OCOC_5H_{11}$ | $(CH_2)_2OCOC_5H_{11}$ |
| 1,4 | $C_{18}H_{37}$ | $C_{18}H_{37}$ | —$CH_2CH_2$—O—$CH_2CH_2$— | |
| 1,3 | $C_{18}H_{37}$ | $C_{18}H_{37}$ | —$CH_2CH_2$—O—$CH_2CH_2$— | |
| 1,4 | n-$C_4H_9$ | $C_{16}H_{33}$ | —$CH_2CH_2$—O—$CH_2CH_2$— | |

*This compound and the remaining compounds are prepared from the corresponding hydroxyalkyl compound by the procedures of Examples VIII - X.

EXAMPLE XXX

1-(Dioctadecyl)Aminomethyl-4-Aminomethyl Benzene

A mixture of 1-(dioctadecylamino)methyl-4-cyanobenzene (11.9 g., 18.7 mM, see Example XXIX), sodium dihydro bis-(2-methoxyethoxy)aluminate (11.0 g. of 70% reagent, 37.5 mM) and benzene (300 ml.) under an atmosphere of nitrogen is refluxed for 40 hours. It is cooled and aqueous sodium hydroxide (50 ml. of 10% solution) is continuously added. The benzene phase is separated, washed with water (2 × 50 ml.) and dried ($Na_2SO_4$). Concentration of the benzene solution gives the product as an oil which solidifies on standing (8.0 g.). It is purified by chromatography on a dry silica gel column and elution with ethyl acetate.

The dihydrochloride salt is obtained by dissolving the product (500 mg.) in chloroform (20 ml.) and adding ethyl acetate saturated with HCl (10 ml.). The salt is filtered, washed with ether, and air dried: 430 mg., m.p. 208°–210° C.

The following compounds are prepared in like manner from appropriate reactants:

| Isomer* | $R_1$ | $R_2$ | Base | Di-HCl M.P. (° C.) |
|---|---|---|---|---|
| 1,3- | $C_{18}H_{37}$ | $C_{18}H_{37}$ | — | 117–8 |
| 1,2- | $C_{18}H_{37}$ | $C_{18}H_{37}$ | — | 90–2 |
| 1,4- | $C_{12}H_{25}$ | $C_{12}H_{25}$ | — | 218–20 |
| 1,4- | 3,4-dihexoxybenzyl | 3,4-dihexoxybenzyl | oil | — |
| 1,4- | 3,4-diisopoxybenzyl | 3,4-diisopoxybenzyl | — | 218–20 |

*continued*

| Isomer* | $R_1$ | $R_2$ | Base | Di-HCl M.P. (° C.) |
|---|---|---|---|---|
| | poxybenzyl | poxybenzyl | | |

*Refers to position of the aminomethyl groups.

EXAMPLE XXXI

The compounds below are prepared by the procedure of Example XXX from the appropriate 1-(substituted amino)methyl cyanobenzenes prepared as intermediates in Example XXIX and from appropriate di(-substituted benzyl)-amines prepared for Examples XXVI and XXVII.

| Isomer | $R_1$ | $R_2$ |
|---|---|---|
| 1,3 | $C_{12}H_{25}$ | $C_{12}H_{25}$ |
| 1,2 | $C_{12}H_{25}$ | $C_{12}H_{25}$ |
| 1,4 | $CH_3$ | $C_{12}H_{25}$ |
| 1,3 | $C_{16}H_{33}$ | $C_{16}H_{33}$ |
| 1,4 | n-$C_4H_9$ | $C_{16}H_{33}$ |
| 1,3 | $C_2H_5$ | $C_{20}H_{41}$ |
| 1,3 | $C_2H_5$ | $C_{14}H_{29}$ |

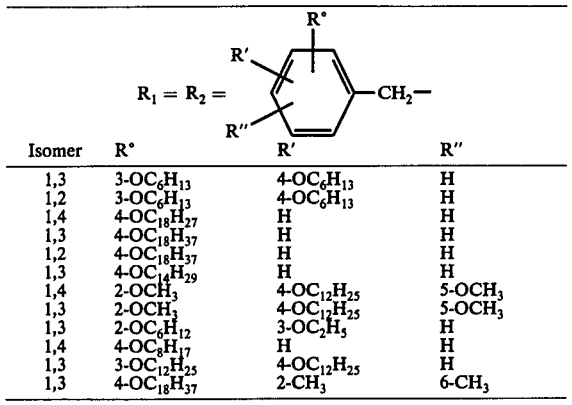

| Isomer | R° | R' | R'' |
|---|---|---|---|
| 1,3 | 3-OC$_6$H$_{13}$ | 4-OC$_6$H$_{13}$ | H |
| 1,2 | 3-OC$_6$H$_{13}$ | 4-OC$_6$H$_{13}$ | H |
| 1,4 | 4-OC$_{18}$H$_{27}$ | H | H |
| 1,3 | 4-OC$_{18}$H$_{37}$ | H | H |
| 1,2 | 4-OC$_{18}$H$_{37}$ | H | H |
| 1,3 | 4-OC$_{14}$H$_{29}$ | H | H |
| 1,4 | 2-OCH$_3$ | 4-OC$_{12}$H$_{25}$ | 5-OCH$_3$ |
| 1,3 | 2-OCH$_3$ | 4-OC$_{12}$H$_{25}$ | 5-OCH$_3$ |
| 1,3 | 2-OC$_6$H$_{12}$ | 3-OC$_2$H$_5$ | H |
| 1,4 | 4-OC$_8$H$_{17}$ | H | H |
| 1,3 | 3-OC$_{12}$H$_{25}$ | 4-OC$_{12}$H$_{25}$ | H |
| 1,3 | 4-OC$_{18}$H$_{37}$ | 2-CH$_3$ | 6-CH$_3$ |

The above products are converted to monoacyl derivatives by the procedure of Example III. By this procedure, the formyl, acetyl and propionyl derivatives are obtained.

EXAMPLE XXXII 1-(substituted amino)methyl-4-hydroxymethyl benzene compounds prepared according to Examples XXV-XXIX are reacted with succinic anhydride, glutaric anhydride, phenyl isocyanate and acyl chlorides as described in Examples VIII, IX and X to give the following compounds:

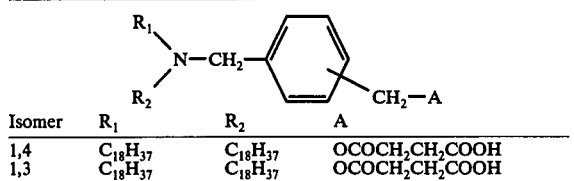

| Isomer | R$_1$ | R$_2$ | A |
|---|---|---|---|
| 1,4 | C$_{18}$H$_{37}$ | C$_{18}$H$_{37}$ | OCOCH$_2$CH$_2$COOH |
| 1,3 | C$_{18}$H$_{37}$ | C$_{18}$H$_{37}$ | OCOCH$_2$CH$_2$COOH |

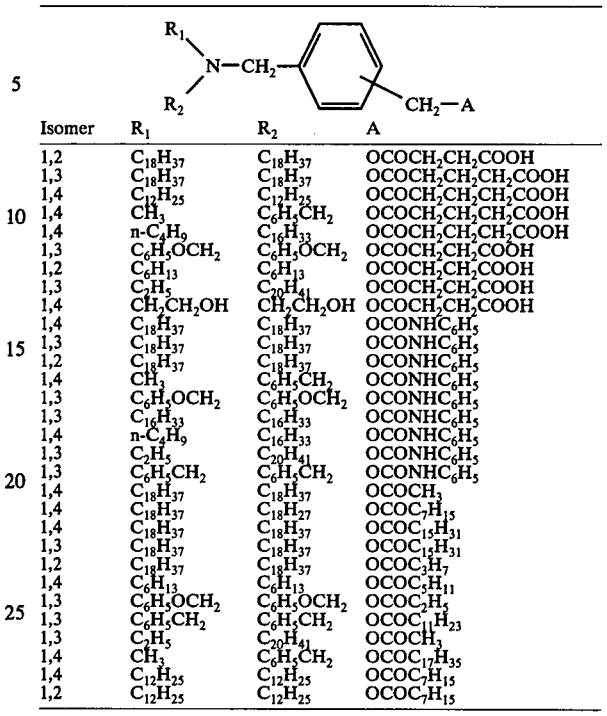

| Isomer | R$_1$ | R$_2$ | A |
|---|---|---|---|
| 1,2 | C$_{18}$H$_{37}$ | C$_{18}$H$_{37}$ | OCOCH$_2$CH$_2$COOH |
| 1,3 | C$_{18}$H$_{37}$ | C$_{18}$H$_{37}$ | OCOCH$_2$CH$_2$CH$_2$COOH |
| 1,4 | C$_{12}$H$_{25}$ | C$_{12}$H$_{25}$ | OCOCH$_2$CH$_2$CH$_2$COOH |
| 1,4 | CH$_3$ | C$_6$H$_5$CH$_2$ | OCOCH$_2$CH$_2$CH$_2$COOH |
| 1,4 | n-C$_4$H$_9$ | C$_{16}$H$_{33}$ | OCOCH$_2$CH$_2$CH$_2$COOH |
| 1,3 | C$_6$H$_5$OCH$_2$ | C$_6$H$_5$OCH$_2$ | OCOCH$_2$CH$_2$COOH |
| 1,2 | C$_6$H$_{13}$ | C$_6$H$_{13}$ | OCOCH$_2$CH$_2$COOH |
| 1,3 | C$_2$H$_5$ | C$_{20}$H$_{41}$ | OCOCH$_2$CH$_2$COOH |
| 1,4 | CH$_2$CH$_2$OH | CH$_2$CH$_2$OH | OCOCH$_2$CH$_2$COOH |
| 1,4 | C$_{18}$H$_{37}$ | C$_{18}$H$_{37}$ | OCONHC$_6$H$_5$ |
| 1,3 | C$_{18}$H$_{37}$ | C$_{18}$H$_{37}$ | OCONHC$_6$H$_5$ |
| 1,2 | C$_{18}$H$_{37}$ | C$_{18}$H$_{37}$ | OCONHC$_6$H$_5$ |
| 1,4 | CH$_3$ | C$_6$H$_5$CH$_2$ | OCONHC$_6$H$_5$ |
| 1,3 | C$_6$H$_5$OCH$_2$ | C$_6$H$_5$OCH$_2$ | OCONHC$_6$H$_5$ |
| 1,3 | C$_{16}$H$_{33}$ | C$_{16}$H$_{33}$ | OCONHC$_6$H$_5$ |
| 1,4 | n-C$_4$H$_9$ | C$_{16}$H$_{33}$ | OCONHC$_6$H$_5$ |
| 1,3 | C$_2$H$_5$ | C$_{20}$H$_{41}$ | OCONHC$_6$H$_5$ |
| 1,3 | C$_6$H$_5$CH$_2$ | C$_6$H$_5$CH$_2$ | OCONHC$_6$H$_5$ |
| 1,4 | C$_{18}$H$_{37}$ | C$_{18}$H$_{37}$ | OCOCH$_3$ |
| 1,4 | C$_{18}$H$_{37}$ | C$_{18}$H$_{27}$ | OCOC$_7$H$_{15}$ |
| 1,4 | C$_{18}$H$_{37}$ | C$_{18}$H$_{37}$ | OCOC$_{15}$H$_{31}$ |
| 1,3 | C$_{18}$H$_{37}$ | C$_{18}$H$_{37}$ | OCOC$_{15}$H$_{31}$ |
| 1,2 | C$_{18}$H$_{37}$ | C$_{18}$H$_{37}$ | OCOC$_3$H$_7$ |
| 1,4 | C$_6$H$_{13}$ | C$_6$H$_{13}$ | OCOC$_5$H$_{11}$ |
| 1,3 | C$_6$H$_5$OCH$_2$ | C$_6$H$_5$OCH$_2$ | OCOC$_7$H$_5$ |
| 1,3 | C$_6$H$_5$CH$_2$ | C$_6$H$_5$CH$_2$ | OCOC$_{11}$H$_{23}$ |
| 1,3 | C$_2$H$_5$ | C$_{20}$H$_{41}$ | OCOCH$_3$ |
| 1,4 | CH$_3$ | C$_6$H$_5$CH$_2$ | OCOC$_{17}$H$_{35}$ |
| 1,4 | C$_{12}$H$_{25}$ | C$_{12}$H$_{25}$ | OCOC$_7$H$_{15}$ |
| 1,2 | C$_{12}$H$_{25}$ | C$_{12}$H$_{25}$ | OCOC$_7$H$_{15}$ |

EXAMPLE XXXIII

The compounds tabulated below are prepared by the procedures of Examples VIII, IX and X from appropriate 1-[bis-(alkoxy benzyl) amino methyl]-4-hydroxymethyl benzenes. These latter compounds are prepared via the procedures of Example XXVI ([bis(alkoxy benzyl)amines]) and Example XXVIII ([1-bis(alkoxy benzyl)aminomethyl]-4-hydroxymethylbenzenes).

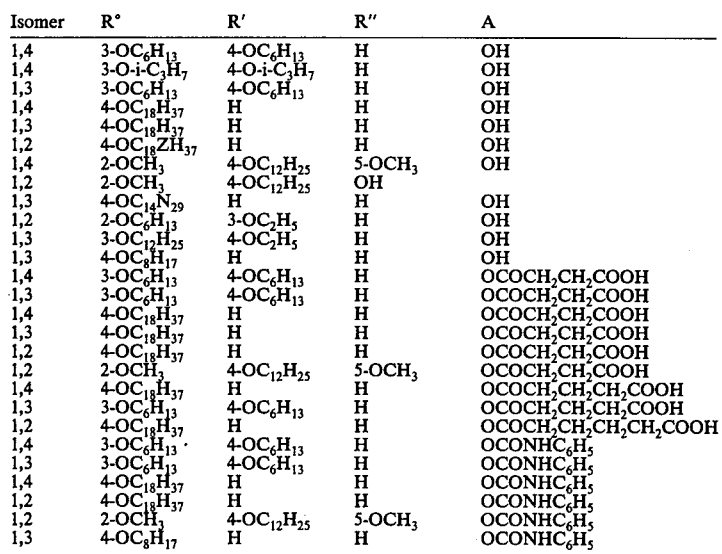

| Isomer | R° | R' | R'' | A |
|---|---|---|---|---|
| 1,4 | 3-OC$_6$H$_{13}$ | 4-OC$_6$H$_{13}$ | H | OH |
| 1,4 | 3-O-i-C$_3$H$_7$ | 4-O-i-C$_3$H$_7$ | H | OH |
| 1,3 | 3-OC$_6$H$_{13}$ | 4-OC$_6$H$_{13}$ | H | OH |
| 1,4 | 4-OC$_{18}$H$_{37}$ | H | H | OH |
| 1,3 | 4-OC$_{18}$H$_{37}$ | H | H | OH |
| 1,2 | 4-OC$_{18}$ZH$_{37}$ | H | H | OH |
| 1,4 | 2-OCH$_3$ | 4-OC$_{12}$H$_{25}$ | 5-OCH$_3$ | OH |
| 1,2 | 2-OCH$_3$ | 4-OC$_{12}$H$_{25}$ | OH | |
| 1,3 | 4-OC$_{14}$N$_{29}$ | H | H | OH |
| 1,2 | 2-OC$_6$H$_{13}$ | 3-OC$_2$H$_5$ | H | OH |
| 1,3 | 3-OC$_{12}$H$_{25}$ | 4-OC$_2$H$_5$ | H | OH |
| 1,3 | 4-OC$_8$H$_{17}$ | H | H | OH |
| 1,4 | 3-OC$_6$H$_{13}$ | 4-OC$_6$H$_{13}$ | H | OCOCH$_2$CH$_2$COOH |
| 1,3 | 3-OC$_6$H$_{13}$ | 4-OC$_6$H$_{13}$ | H | OCOCH$_2$CH$_2$COOH |
| 1,4 | 4-OC$_{18}$H$_{37}$ | H | H | OCOCH$_2$CH$_2$COOH |
| 1,3 | 4-OC$_{18}$H$_{37}$ | H | H | OCOCH$_2$CH$_2$COOH |
| 1,2 | 4-OC$_{18}$H$_{37}$ | H | H | OCOCH$_2$CH$_2$COOH |
| 1,2 | 2-OCH$_3$ | 4-OC$_{12}$H$_{25}$ | 5-OCH$_3$ | OCOCH$_2$CH$_2$COOH |
| 1,4 | 4-OC$_{18}$H$_{37}$ | H | H | OCOCH$_2$CH$_2$CH$_2$COOH |
| 1,3 | 3-OC$_6$H$_{13}$ | 4-OC$_6$H$_{13}$ | H | OCOCH$_2$CH$_2$CH$_2$COOH |
| 1,2 | 4-OC$_{18}$H$_{37}$ | H | H | OCOCH$_2$CH$_2$CH$_2$CH$_2$COOH |
| 1,4 | 3-OC$_6$H$_{13}$ | 4-OC$_6$H$_{13}$ | H | OCONHC$_6$H$_5$ |
| 1,3 | 3-OC$_6$H$_{13}$ | 4-OC$_6$H$_{13}$ | H | OCONHC$_6$H$_5$ |
| 1,4 | 4-OC$_{18}$H$_{37}$ | H | H | OCONHC$_6$H$_5$ |
| 1,2 | 4-OC$_{18}$H$_{37}$ | H | H | OCONHC$_6$H$_5$ |
| 1,2 | 2-OCH$_3$ | 4-OC$_{12}$H$_{25}$ | 5-OCH$_3$ | OCONHC$_6$H$_5$ |
| 1,3 | 4-OC$_8$H$_{17}$ | H | H | OCONHC$_6$H$_5$ |

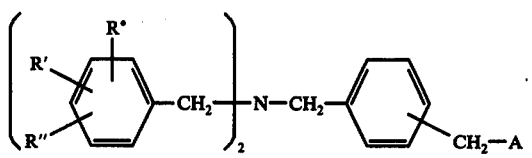

| Isomer | R° | R' | R'' | A |
|---|---|---|---|---|
| 1,4 | 3-O-i-C3H7 | 4-O-i-C3H7 | H | OCONHC6H5 |
| 1,4 | 4-OC18H37 | H | H | OCOCH3 |
| 1,3 | 4-OC18H37 | H | H | OCOCH3 |
| 1,4 | 4-OC18H37 | H | H | OCOC7H15 |
| 1,3 | 4-OC18H37 | H | H | OCOC15H31 |
| 1,4 | 4-OC8H17 | H | H | OCOC7H15 |
| 1,2 | 4-OC18H37 | H | H | OCOC3H7 |
| 1,2 | 2-OC6H13 | 3-OC2H5 | H | OCOC9H19 |
| 1,4 | 2-OCH3 | 4-OC12H25 | 5-OCH3 | OCOC17H35 |
| 1,4 | 4-OC18H37 | H | H | Cl |
| 1,4 | 4-OC8H17 | H | H | Cl |
| 1,3 | 4-OC18H37 | H | H | Cl |
| 1,3 | 3-OC6H13 | 4-OC6H13 | H | Cl |
| 1,4 | 4-OC8H17 | H | H | Br |
| 1,2 | 2-OCH3 | 4-OC12H25 | 5-OCH3 | Br |
| 1,2 | 2-OC6H13 | 3-OC2H5 | H | Br |
| 1,4 | 3-OC6H13 | 4-OC6H13 | H | Cl |
| 1,4 | 3-O-i-C3H7 | 4-O-i-C3H7 | H | Cl |
| 1,2 | 4-OC18H37 | H | H | Cl |
| 1,4 | 2-OCH3 | 4-OC12H25 | 5-OCH3 | Br |
| 1,3 | 4-OC14H29 | H | H | Br |
| 1,3 | 3-OC12H25 | 4-OC2H5 | H | Br |
| 1,3 | 4-OC8H17 | H | H | Cl |

EXAMPLE XXXIV

[1-Bis(Alkoxybenzyl)Aminomethyl]-Alkylthiomethyl Benzenes

A solution of the appropriate [1-bis(alkoxybenzyl-)aminomethyl]-chloromethyl (or bromomethyl) benzene (Example XXXIV) in N,N-dimethylformamide and at least one equivalent of the appropriate sodium alkylsulfide (prepared from the appropriate mercaptan and sodium hydride) is stirred for 16–20 hours at 40°–60° C. The mixture is diluted with four volumes of water and extracted with hexane. The extract is dried (Na2SO4) and evaporated to give the crude product. Purification is achieved by column chromatography on silica gel. The charged column is eluted first with benzene to remove unreacted starting material and then with ethyl acetate or methanol to elute the product which is recovered by evaporation of the eluate.

The following compounds are thus prepared:

| Isomer | R° | R' | R'' | S-alkyl alkyl |
|---|---|---|---|---|
| 1,4 | 4-OC18H37 | H | H | CH3 |
| 1,4 | 4-OC18H37 | H | H | C6H13 |
| 1,4 | 4-OC18H37 | H | H | C18H37 |
| 1,3 | 4-OC18H37 | H | H | C6H13 |
| 1,3 | 4-OC18H37 | H | H | C18H37 |
| 1,3 | 4-OC18H37 | H | H | i-C3H7 |
| 1,2 | 4-OC18H37 | H | H | C6H13 |
| 1,4 | 4-OC8H17 | H | H | C12H25 |
| 1,3 | 3-OC6H13 | 4-OC6H13 | H | C2H5 |
| 1,3 | 3-OC6H13 | 4-OC6H13 | H | C12H25 |
| 1,2 | 2-OCH3 | 4-OC12H25 | 5-OCH3 | CH3 |
| 1,2 | 2-OCH3 | 4-OC12H25 | 5-OCH3 | C4H9 |
| 1,2 | 2-OCH3 | 4-OC12H25 | 5-OCH3 | C16H33 |
| 1,2 | 2-OC6H13 | 3-OC2H5 | H | C2H5 |
| 1,2 | 2-OC6H13 | 3-OC2H5 | H | C14H29 |
| 1,4 | 3-OC6H13 | 4-OC6H13 | H | C12H25 |
| 1,4 | 3-O-i-C3H7 | 4-O-i-C3H7 | H | i-C3H7 |
| 1,4 | 3-O-i-C3H7 | 4-O-i-C3H7 | H | C12H25 |

| Isomer | R° | R' | R'' | S-alkyl alkyl |
|---|---|---|---|---|
| 1,4 | 3,4-O—O—CH2—O— | | H | C2H5 |
| 1,4 | 2-OCH3 | 4-OC12H25 | 5-OCH3 | C3H7 |
| 1,4 | 2-OCH3 | 4-OC12H25 | 5-OCH3 | C8H17 |
| 1,3 | 4-OC14H29 | 4-OC12H25 | 5-OCH3 | C6H13 |
| 1,3 | 4-OC14H29 | 4-OC12H25 | 5-OCH3 | C16H33 |
| 1,3 | 3-OC12H25 | 4-OC2H5 | H | CH3 |
| 1,3 | 3-OC12H25 | 4-OC2H5 | H | C10H21 |
| 1,3 | 4-OC8H17 | H | H | C6H13 |
| 1,3 | 4-OC8H17 | H | H | C14H29 |

EXAMPLE XXXV

[1-Bis(Alkoxybenzyl)Aminomethyl]-Alkoxymethyl Benzenes

The procedure of Example XXXIV is repeated using the appropriate sodium alkoxide in place of a sodium alkyl sulfide to give the following compounds:

| Isomer | R° | R' | R'' | O-alkyl alkyl |
|---|---|---|---|---|
| 1,4 | 4-OC18H37 | H | H | CH3 |
| 1,4 | 4-OC18H37 | H | H | C6H13 |
| 1,4 | 4-OC18H37 | H | H | C18H37 |
| 1,3 | 4-OC18H37 | H | H | C6H13 |
| 1,3 | 4-OC18H37 | H | H | C18H37 |
| 1,2 | 4-OC18H37 | H | H | C6H13 |
| 1,2 | 4-OC18H37 | H | H | C14H29 |
| 1,4 | 4-OC8H17 | H | H | C12H25 |
| 1,3 | 3-OC6H13 | 4-OC6H13 | H | i-C3H7 |
| 1,2 | 2-OCH3 | 4-OC12H25 | 5-OCH3 | CH3 |
| 1,2 | 2-OCH3 | 4-OC12H25 | 5-OCH3 | C6H13 |
| 1,2 | 2-OCH3 | 4-OC12H25 | 5-OCH3 | C16H33 |

-continued

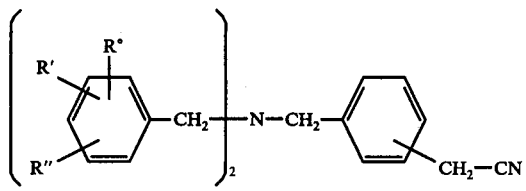

| Isomer | R° | R' | R'' | alkyl |
|---|---|---|---|---|
| 1,4 | 3-OC$_6$H$_{13}$ | 4-OC$_6$H$_{13}$ | H | C$_6$H$_{13}$ |
| 1,4 | 3-O-i-C$_3$H$_7$ | 4-O-i-C$_3$H$_7$ | H | C$_2$H$_5$ |
| 1,4 | 3-O-i-C$_3$H$_7$ | 4-O-i-C$_3$H$_7$ | H | C$_{14}$H$_{29}$ |
| 1,3 | 4-OC$_{14}$H$_{29}$ | H | H | C$_4$H$_9$ |
| 1,4 | 2-OCH$_3$ | 4-OC$_{12}$H$_{25}$ | 5-OCH$_3$ | C$_3$H$_7$ |
| 1,4 | 2-OCH$_3$ | 4-OC$_{12}$H$_{25}$ | 5-OCH$_3$ | C$_{10}$H$_{21}$ |
| 1,3 | 3-OC$_{12}$H$_{25}$ | 4-OC$_2$H$_5$ | H | CH$_3$ |
| 1,3 | 3-OC$_{12}$H$_{25}$ | 4-OC$_2$H$_5$ | H | C$_6$H$_{13}$ |
| 1,3 | 3-OC$_{12}$H$_{25}$ | 4-OC$_2$H$_5$ | H | C$_{16}$H$_{33}$ |
| 1,3 | 4-OC$_8$H$_{17}$ | H | H | C$_6$H$_{13}$ |

EXAMPLE XXXVI

[1-Bis(Alkoxybenzyl)Aminomethyl]-Cyanomethyl Benzenes

A solution of the appropriate [1-bis(alkoxybenzyl)aminomethyl]-chloro(or bromo)methylbenzene in N,N-dimethylformamide and potassium cyanidepotassium iodide (5 equivalents of each) is stirred at 60°–100° C. for 24 hours. The mixture is diluted with water (4–5 volumes) and extracted with hexane. The extract is dried (Na$_2$SO$_4$) and evaporated to give the crude product. It is purified by columm chromatography as in Example XXXIV In this manner the chloro and bromo compounds of Example XXXIII are converted to the corresponding cyano derivatives of the formula:

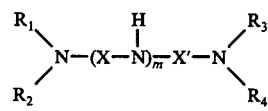

EXAMPLE XXXVII

[1-Bis(Alkoxybenzyl)Aminomethyl]-Alkanoylthiomethyl Benzenes

A solution of equimolar amounts of the appropriate [1-bis-(alkoxybenzyl)aminomethyl]-chloro(or bromo)-methylbenzene (Example XXXIII) and the sodium salt of the appropriate thiocarboxylic acid in N,N-dimethylformamide is stirred for 16–20 hours at 60° C. The reaction mixture is cooled, diluted with 3–4 volumes of water and extracted with hexane. The extract is dried (Na$_2$SO$_4$) and evaporated to give the crude product. It is purified by column chromatography according to the procedure of Example XXXIV.

The following compounds are thus prepared:

| Isomer | R° | R' | R'' | A'' |
|---|---|---|---|---|
| 1,4 | 4-OC$_{18}$H$_{37}$ | H | H | CH$_3$CO |
| 1,4 | 4-OC$_8$H$_{17}$ | H | H | C$_7$H$_{15}$CO |
| 1,3 | 4-OC$_{18}$H$_{37}$ | H | H | C$_{11}$H$_{23}$CO |
| 1,3 | 3-OC$_6$H$_{13}$ | 4-OC$_6$H$_{13}$ | H | C$_2$H$_5$CO |
| 1,4 | 4-OC$_8$H$_{17}$ | H | H | C$_9$H$_{19}$CO |
| 1,2 | 2-OCH$_3$ | 4-OC$_{12}$H$_{25}$ | 5-OCH$_3$ | C$_3$H$_7$CO |
| 1,2 | 2-OC$_6$H$_{13}$ | 3-OC$_2$H$_5$ | H | C$_7$H$_{15}$CO |
| 1,4 | 4-OC$_{18}$H$_{37}$ | H | H | C$_{17}$H$_{35}$CO |
| 1,3 | 3-OC$_6$H$_{13}$ | 4-OC$_6$H$_{13}$ | H | n-C$_4$H$_9$CO |
| 1,2 | 2-OCH$_3$ | 4-OC$_{12}$H$_{25}$ | 5-OCH$_3$ | C$_{11}$H$_{23}$CO |
| 1,3 | 4-OC$_8$H$_{17}$ | H | H | n-C$_4$H$_9$CO |
| 1,4 | 3-OC$_6$H$_{13}$ | 4-OC$_6$H$_{13}$ | H | C$_{16}$H$_{33}$CO |
| 1,4 | 3-OC$_6$H$_{13}$ | 4-OC$_6$H$_{13}$ | H | C$_3$H$_7$CO |
| 1,4 | 3-O-i-C$_3$H$_7$ | 4-O-i-C$_3$H$_7$ | H | C$_{11}$H$_{23}$CO |
| 1,2 | 4-OC$_{18}$H$_{37}$ | H | H | C$_7$H$_{15}$CO |
| 1,4 | 2-OCH$_3$ | 4-OC$_{12}$H$_{25}$ | 5-OCH$_3$ | C$_9$H$_{19}$CO |
| 1,3 | 4-OC$_{14}$H$_{29}$ | H | H | C$_{11}$H$_{23}$CO |
| 1,3 | 3-OC$_{12}$H$_{25}$ | 4-OC$_2$H$_5$ | H | C$_{13}$H$_{27}$CO |
| 1,3 | 4-OC$_8$H$_{17}$ | H | H | C$_{13}$H$_{27}$CO |

What is claimed is:

1. A process for combating viral infections in vertebrate animals which comprises parenterally, intranasally, or topically administering to the animals an antivirally effective amount of a composition containing as the essential active ingredient a compound selected from the group consisting of those having the formula $$R_1 \diagdown N-(X-N)_m-X'-N \diagup R_3$$
$$R_2 \diagup \phantom{N-(X-N)_m-X'-N} \diagdown R_4$$

with H on the central N and the non-toxic acid addition salts thereof wherein
 R$_1$ and R$_2$ are each alkyl of from 12 to 18 carbon atoms;
 R$_3$ and R$_4$ are each hydrogen;
 X' is phenylenedimethylene; and
 m is 0.

2. The process of claim 1 wherein X' is meta-phenylenedimethylene.

3. The process of claim 2 wherein the compound is 1-di-(n-octadecyl)aminomethyl-3-aminomethylbenzene, the compound wherein each of R$_1$ and R$_2$ is n-octadecyl; and each of R$_3$ and R$_4$ is hydrogen.

4. The process of claim 2 wherein the compound is 1-di-(n-hexadecyl)aminomethyl-3-aminomethylbenzene, the compound wherein each of R$_1$ and R$_2$ is n-hexadecyl; and each of R$_3$ and R$_4$ is hydrogen.

* * * * *